(12) United States Patent
Aoki et al.

(10) Patent No.: US 8,501,949 B2
(45) Date of Patent: Aug. 6, 2013

(54) TETOMILAST POLYMORPHS

(75) Inventors: Satoshi Aoki, Tokushima (JP); Kenji Nakaya, Tokushima (JP); Masahiro Sota, Tokushima (JP); Masashi Ishigami, Yoshinogari (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 697 days.

(21) Appl. No.: 12/086,587

(22) PCT Filed: Mar. 15, 2007

(86) PCT No.: PCT/JP2007/055931
§ 371 (c)(1),
(2), (4) Date: May 17, 2010

(87) PCT Pub. No.: WO2007/119496
PCT Pub. Date: Oct. 25, 2007

(65) Prior Publication Data
US 2010/0222590 A1  Sep. 2, 2010

(30) Foreign Application Priority Data
Mar. 17, 2006  (JP) .................................. 2006-075307

(51) Int. Cl.
C07D 417/04  (2006.01)

(52) U.S. Cl.
USPC ..................................................... 546/270.4

(58) Field of Classification Search
USPC ....................................... 546/270.4; 514/342
See application file for complete search history.

(56) References Cited

U.S. PATENT DOCUMENTS

| 5,314,506 A | 5/1994 | Midler, Jr. et al. |
| 6,221,153 B1 | 4/2001 | Castor |
| 6,627,646 B2 * | 9/2003 | Bakale et al. ................. 514/322 |

FOREIGN PATENT DOCUMENTS

| EP | 0 513 387 A1 | 11/1992 |
| JP | 2000-229920 | 8/2000 |
| WO | WO-98/14191 | 4/1998 |
| WO | WO 00/32189 | 6/2000 |
| WO | WO 01/23377 A2 | 4/2001 |
| WO | WO-03/009844 A1 | 2/2003 |
| WO | WO 03/026659 A1 | 4/2003 |
| WO | WO 2005/058835 A2 | 6/2005 |

OTHER PUBLICATIONS

U.S. Pharmacopia #23, National Formulary #18, 1995, 1843-1844.*
Concise Encyclopedia Chemistry, NY: Walter de Gruyter, 1993, 872-873.*
Muzaffar et al., "Polymorphism and Drug Availability, etc.," J of Pharm. (Lahore), 1979, 1(1), 59-66.*
Doelker, english translation of Ann. Pharm. Fr., 2002, 60: 161-176, pp. 1-39.*
Doelker, english translation of S.T.P, Pratiques (1999), 9(5), 399-409, pp. 1-33.*
Singhal et al., "Drug Polymorphism, etc.," Advanced Drug Delivery reviews 56, p. 335-347 (2004).*
CMU Pharmaceutical polymorphism, internet, p. 1-3 (2002) (print out Apr. 3, 2008).*
Otuska et al., "Effect of Polymorphic, etc.," Chem. Pharm. Bull., 47(6) 852-856 (1999).*
Taday et al., "Using Terahertz, etc.," J of Pharm. Sci., 92(4), 2003, 831-838.*
Office Action dated Feb. 11, 2010 in corresponding Australian application (2007239906).
M. Caira, Topics in Current Chemistry, 1998 vol. 198, pp. 163-208.
Chihiro et al.; "Novel Thiazole Derivatives as Inhibitors of Superoxide Production by Human Neutrophils: Synthesis and Structure-Activity Relationships"; J. Med. Chem., vol. 38, pp. 353-358, (1995).
Brittain, H.G. and Dekker, M. (eds.), "Polymorphism in pharmaceutical solids," (1999); Chapter 1 (Grant), p. 1-10.
J. Keith Guillory, "Generation of Polymorphs, Hydrates, Solvates, and Amorphous Solids, (Chapter 5) of "Polymorphism in Pharmaceutical Solids, Drugs and the Pharmaceutical Sciences, 1999, vol. 95, pp. 183-226.
N. K. Jain et al., Polymorphism in Pharmacy, Indian Drugs, 1986, vol. 23, No. 6, pp. 315-329.
S. R. Byrn et al., "Solid-State Pharmaceutical Chemistry," Chemistry of Materials, Jul. 1994, vol. 6, No. 7, pp. 1148-1158.
Office Action issued May 4, 2011 in Israeli Patent Application No. 192237.
Office Action corresponding Taiwanese application 96108801.
Furniss, Brian S. et al., Vogel's Textbook of Practical Organic Chemistry, May 8, 2008, p. 136.

* cited by examiner

Primary Examiner — Patricia L Morris
(74) Attorney, Agent, or Firm — Finnegan, Henderson, Farabow, Garrett & Dunner, L.L.P.

(57) ABSTRACT

The present invention provides a tetomilast crystal that is industrially easily produced in a large volume. (1) a tetomilast hydrate crystal having a powder X-ray diffraction spectrum that is substantially the same as the powder X-ray diffraction spectrum shown in FIG. 2; (2) an anhydrous tetomilast type A crystal having a powder X-ray diffraction spectrum that is substantially the same as the powder X-ray diffraction spectrum shown in FIG. 4; (3) an anhydrous tetomilast type C crystal having a powder X-ray diffraction spectrum that is substantially the same as the powder X-ray diffraction spectrum shown in FIG. 8; (4) a tetomilast acetonitrile solvate crystal having a powder X-ray diffraction spectrum that is substantially the same as the powder X-ray diffraction spectrum shown in FIG. 10; and (5) a mixture consisting of the above anhydrous tetomilast type A crystal and an anhydrous tetomilast type B crystal. These crystals are stable towards heat and moisture, and are also excellent in terms of the disintegration property and dissolution property of tablets. Accordingly, these crystals are preferably used as pharmaceutical compositions.

14 Claims, 14 Drawing Sheets

TETOMILAST POLYMORPHS

TECHNICAL FIELD

The present invention relates to a novel tetomilast crystal.

BACKGROUND ART 2-(3,4-diethoxyphenyl)-4-(2-carboxy-6-pyridyl)thiazole (or 6-[2-(3,4-diethoxyphenyl)thiazol-4-yl]pyridin-2-carboxylic acid) is a known compound. This compound is named as tetomilast. This tetomilast has active oxygen inhibitory action, cytokine generation inhibitory action, adhesion inhibitory action, etc., and it is useful for the treatment of ulcerative colitis, Crohn's disease, asthma, and the like (JP-A-5-51318 (paragraph [0015], Example 371) and JP-A-10-152437 (paragraphs [0024] and [0029]). In addition, tetomilast is also useful as a therapeutic agent for chronic obstructive pulmonary disease (JP-A-2003-104890). Moreover, such a tetomilast crystal is stable towards heat and moisture, and is excellent in terms of the disintegration property and dissolution property of tablets.

According to Example 371 of JP-A-5-51318, an anhydrous tetomilast crystal (hereinafter referred to as an "anhydrous tetomilast type B crystal") is produced by allowing 3,4-diethoxythiobenzamide to react with 2-(2-chloroacetyl)-6-pyridine carboxylic acid and then recrystallizing the obtained tetomilast crude product from ethanol, for example.

Furthermore, according to Journal of Medicinal Chemistry, 1995, 38, pp. 353-358, such an anhydrous tetomilast type B crystal is produced by allowing 3,4-diethoxythiobenzamide to react with 2-(2-bromoacetyl)-6-pyridine carboxylic acid, then hydrolyzing the obtained methyl 6-[2-(3,4-diethoxyphenyl)thiazol-4-yl]pyridin-2-carboxylic acid methyl ester, and then recrystallizing the obtained tetomilast crude product from ethyl acetate.

However, since an anhydrous tetomilast type B crystal has the property of causing clogging, if such an anhydrous tetomilast type B crystal is produced by the conventional recrystallization method, an operating efficiency significantly deteriorates during filtration. Thus, it is difficult to produce anhydrous tetomilast type B crystals industrially in a large volume. Accordingly, it is strongly desired that a novel tetomilast crystal, which is advantageous in terms of industrial mass production, be developed.

DISCLOSURE OF THE INVENTION

It is a main object of the present invention to provide a novel tetomilast crystal that is industrially produced in a large volume.

The present inventors have conducted intensive studies directed towards achieving the aforementioned object. As a result, the inventors have found that a novel tetomilast crystal, which can be produced industrially in a large volume, can be obtained by stirring anhydrous tetomilast type B crystals in an aqueous solvent, and that the above tetomilast crystal is further recrystallized using a suitable solvent, or is further heated while it is suspended in a specific solvent, so as to obtain a tetomilast crystal having various physical properties. The present invention has been completed based on these findings.

That is to say, the present invention relates to the following tetomilast crystal and pharmaceutical composition:

1. A tetomilast hydrate crystal having a powder X-ray diffraction spectrum that is substantially the same as the powder X-ray diffraction spectrum shown in FIG. 2.
2. An anhydrous tetomilast type A crystal having a powder X-ray diffraction spectrum that is substantially the same as the powder X-ray diffraction spectrum shown in FIG. 4.
3. An anhydrous tetomilast type C crystal having a powder X-ray diffraction spectrum that is substantially the same as the powder X-ray diffraction spectrum shown in FIG. 8.
4. A tetomilast acetonitrile solvate crystal having a powder X-ray diffraction spectrum that is substantially the same as the powder X-ray diffraction spectrum shown in FIG. 10.
5. A mixture of the anhydrous tetomilast type A crystal described in item 2 and an anhydrous tetomilast type B crystal.
6. A pharmaceutical composition comprising at least one type of tetomilast crystal selected from the group consisting of a tetomilast hydrate crystal, an anhydrous tetomilast type A crystal, an anhydrous tetomilast type C crystal, and a tetomilast acetonitrile solvate crystal.
7. The pharmaceutical composition according to item 6, which is an agent for preventing and/or treating gastrointestinal ulcer, an agent for preventing and/or treating cardiacischemic disease, an agent for preventing and/or treating cerebrovascular disease, a liver and kidney function improver used for disorders caused by transplantation, microcirculation failure, etc., or an agent for preventing and/or treating Behcet's disease, cutaneous vasculitis, ulcerative colitis, malignant rheumatism, arthritis, arteriosclerosis or diabetes.
8. The pharmaceutical composition according to item 6, which is an agent for preventing and/or treating chronic rheumatoid arthritis, endotoxin shock, ARDS, thermal burn, asthma, chronic heart failure, myocardial infarction, viral myocarditis, or an agent for preventing and/or treating ischemic reperfusion abnormality, transition from SIRS (systemic inflammatory response syndrome) to organ failure, multiple organ failure, inflammatory bowel disease, autoimmune disease, metastasis, immunological rejection occurring during transplantation, monoclonal B cell abnormality, polyclonal B cell abnormality, atrial myxoma, Castleman's syndrome, primary glomerulonephritis, mesangial proliferative nephritis, cancer cachexia, Lennert's lymphoma, psoriasis, atopic dermatitis, Kaposi's sarcoma developed due to AIDS, postmenopausal osteoporosis, septicemia, inflammatory disease or chronic obstructive pulmonary disease.
9. The pharmaceutical composition according to item 8, wherein the inflammatory intestinal disease is ulcerative colitis or Crohn's disease.
10. The pharmaceutical composition according to item 8, which is an agent for preventing and/or treating chronic obstructive pulmonary disease.
11. A process for the preparation of a tetomilast hydrate, which is characterized in that it comprises stirring an anhydrous tetomilast type B crystal in an aqueous solvent.
12. A process for the preparation of an anhydrous tetomilast type A crystal, which is characterized in that it comprises recrystallization from a solution formed by dissolving an anhydrous tetomilast type B crystal in a solvent.
13. The process according to item 12, wherein the solvent is ethanol, acetone, or acetone-water (wherein the acetone content is 40% or more).
14. A process for the preparation of an anhydrous tetomilast type A crystal, which is characterized in that it comprises recrystallization from a solution formed by dissolving in a solvent at least one type of tetomilast crystal selected from the group consisting of a tetomilast hydrate crystal, an anhydrous tetomilast type C crystal, and a tetomilast acetonitrile solvate crystal.

15. The process according to item 14, wherein the solvent is a mixed solvent consisting of water, and at least one organic solvent selected from the group consisting of methanol, ethanol, acetone, and tetrahydrofuran.
16. A process for the preparation of an anhydrous tetomilast type C crystal, which is characterized in that it comprises recrystallization from a solution formed by dissolving an anhydrous tetomilast type B crystal in a solvent.
17. The process according to item 16, wherein the solvent is methanol or ethanol.
18. A process for the preparation of an anhydrous tetomilast type C crystal, which is characterized in that it comprises recrystallization from a solution formed by dissolving in a solvent at least one type of tetomilast crystal selected from the group consisting of a tetomilast hydrate crystal, an anhydrous tetomilast type A crystal, and a tetomilast acetonitrile solvate crystal.
19. The production method according to item 18, wherein the solvent is methanol or ethanol.
20. A process for the preparation of a tetomilast acetonitrile solvate crystal, which is characterized in that it comprises recrystallization from a solution formed by dissolving an anhydrous tetomilast type B crystal in acetonitrile.
21. A process for the preparation of an anhydrous tetomilast acetonitrile solvate crystal, which is characterized in that it comprises recrystallization from a solution formed by dissolving in a solvent at least one type of tetomilast crystal selected from the group consisting of a tetomilast hydrate crystal, an anhydrous tetomilast type A crystal, and an anhydrous tetomilast type C crystal.
22. A process for the preparation of a mixture consisting of an anhydrous tetomilast type A crystal and an anhydrous tetomilast type B crystal, which is characterized in that it comprises recrystallization from a solution formed by dissolving the anhydrous tetomilast type B crystal in a solvent.
23. The process according to item 22, wherein the solvent is acetone-water (wherein the acetone content is 40% to 95% by volume).
24. A process for the preparation of a mixture consisting of an anhydrous tetomilast type A crystal and an anhydrous tetomilast type B crystal, which is characterized in that it comprises recrystallization from a solution formed by dissolving in a solvent at least one type of tetomilast crystal selected from the group consisting of a tetomilast hydrate crystal, an anhydrous tetomilast type A crystal, a tetomilast acetonitrile solvate crystal, and an anhydrous tetomilast type C crystal.
25. The process according to item 24, wherein the solvent is acetone-water (wherein the acetone content is 40% to 95% by volume).

In the present invention, the term "novel tetomilast crystals" is used to mean a tetomilast hydrate crystal, an anhydrous tetomilast type A crystal, an anhydrous tetomilast type C crystal, a tetomilast acetonitrile solvate crystal, and a mixture of an anhydrous tetomilast type A crystal and an anhydrous tetomilast type B crystal.

In addition, in the present invention, the term "tetomilast crystal" is used to simply mean a generic name for such novel tetomilast crystals and an anhydrous tetomilast type B crystal that is a known as a tetomilast crystal.

BEST MODE FOR CARRYING OUT THE INVENTION

Tetomilast Hydrate Crystal

Figure 1:
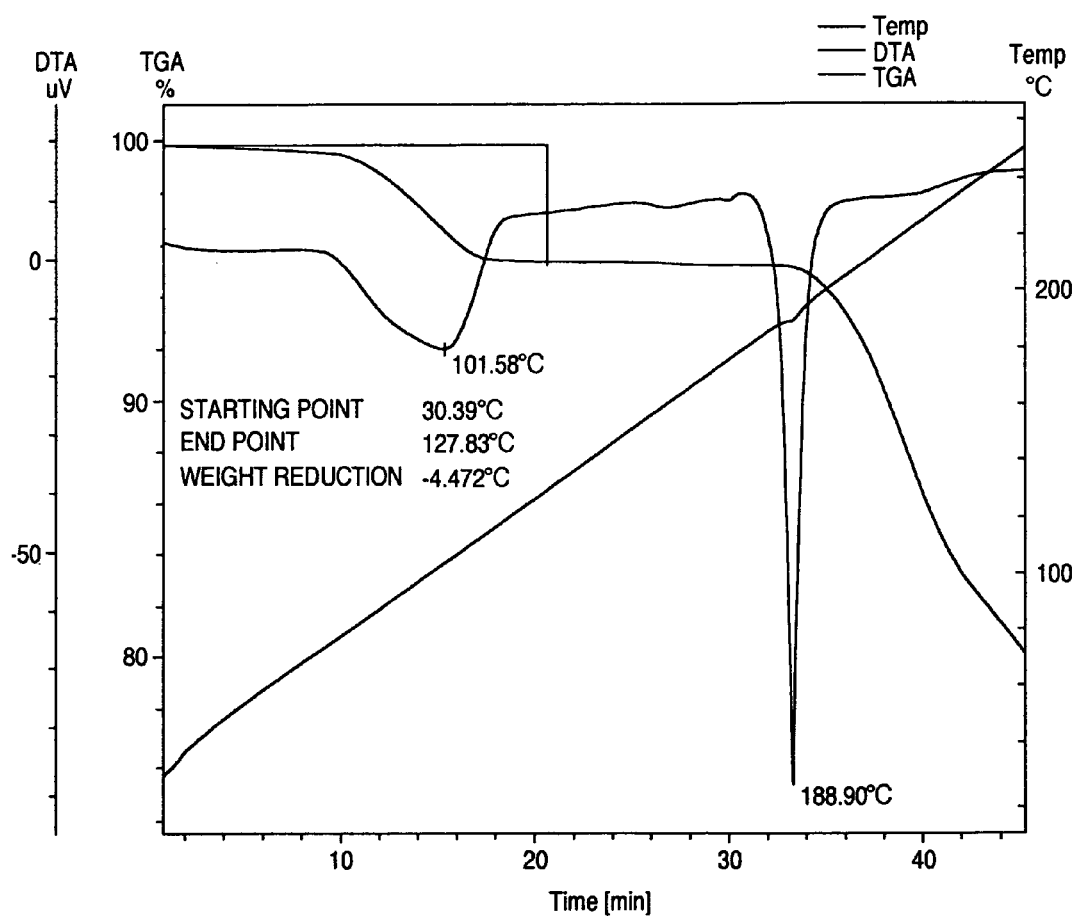
FIG. 1 is a view showing the thermogravimetry/differential thermal analysis of the tetomilast hydrate crystal obtained in Example 5 (1)

The tetomilast hydrate crystal of the present invention includes 0.5 to 3 hydrate crystals. Among the tetomilast hydrate crystals of the present invention, a monohydrate crystal has the physicochemical properties described in (1) to (3) below:

(1) The monohydrate crystal has an endothermic curve that is substantially the same as the thermogravimetry/differential thermal analysis (temperature-rising rate/min) endothermic curve shown in FIG. 1. Specifically, such a monohydrate crystal is characterized in that it has an endothermic peak around 189° C. and a wide peak around 102° C.

Figure 2:
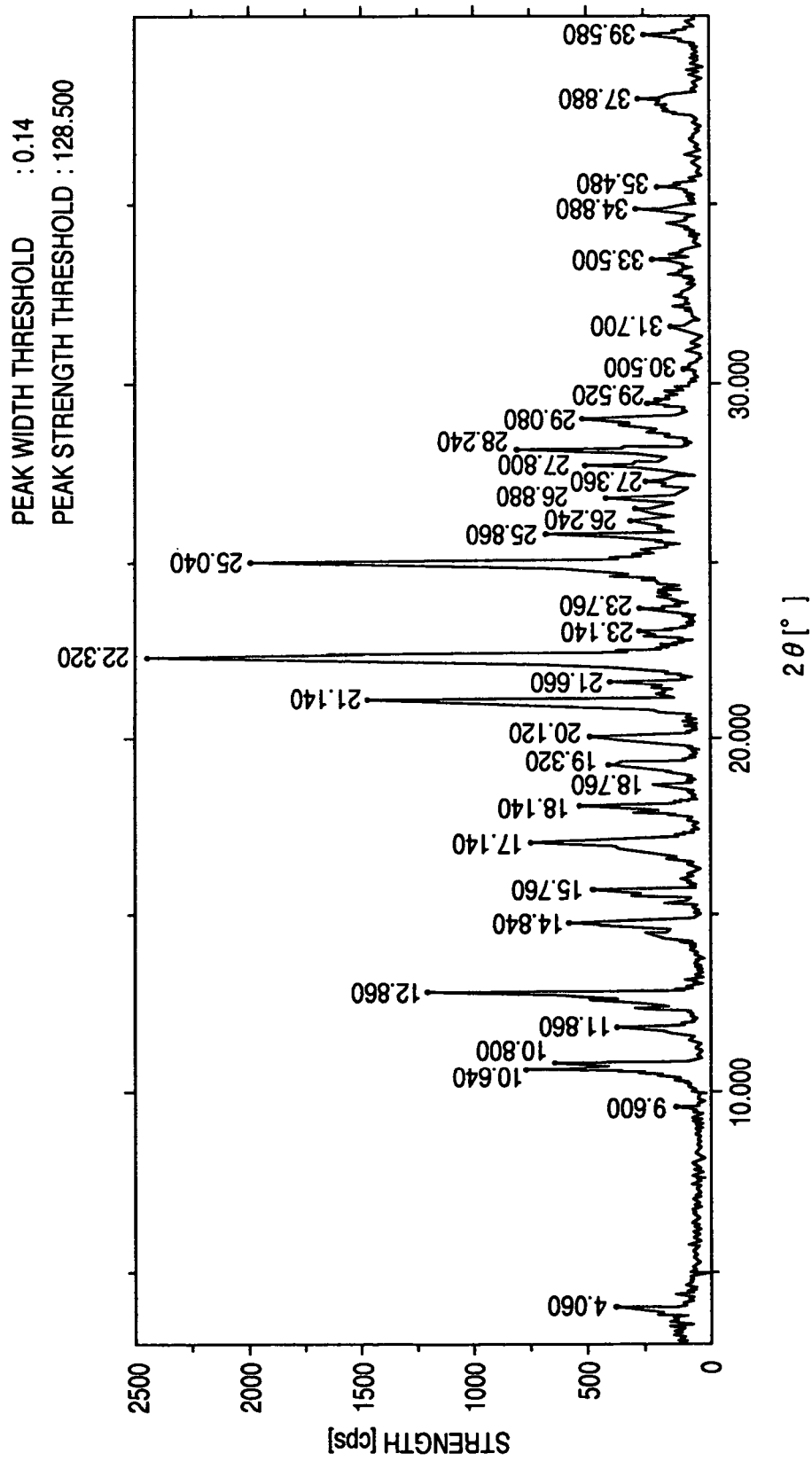
FIG. 2 is a view showing the powder X-ray diffraction of the tetomilast hydrate crystal obtained in Example 5 (1)

(2) The monohydrate crystal has a powder X-ray diffraction spectrum that is substantially the same as the powder X-ray diffraction spectrum shown in FIG. 2. Specifically, it has characteristic peaks at $2\theta=10.6°, 12.9°, 21.1°, 22.3°$, and $25.0°$.

(3) The monohydrate crystal has significant infrared absorption bands at 3516, 3433, 1742, 1709, 1587, 1472, 1267, 1143, 1040, 758, and 716 $cm^{-1}$ in the IR (KBr) spectrum.

Method for Producing Tetomilast Hydrate Crystal

The tetomilast hydrate crystal of the present invention can be obtained by stirring in an aqueous solvent the known anhydrous tetomilast type B crystal or an anhydrous tetomilast type B crystal obtained by the method as described below.

Such an aqueous solvent is a mixed solvent obtained by mixing an organic solvent such as methanol, ethanol, isopropanol, acetone, or ethylmethylketone, with water. Examples of such a mixed solvent may include methanol-water (a methanol content of 10% to 80% by volume), ethanol-water (an ethanol content of 10% to 70% by volume), isopropanol-water (an isopropanol content of 10% to 60% by volume), acetone-water (an acetone content of 10% to 80% by volume), and ethylmethylketone-water (an ethylmethylketone content of 10% to 80% by volume). Of these, acetone-water (an acetone content of 10% to 60% by volume) and ethylmethylketone-water (an ethylmethylketone content of 10% to 60% by volume) are particularly preferable. Acetone-water (an acetone content of 35% to 55% by volume) is more preferable.

The amount of an aqueous solvent used is not limited. It is used in an amount of at least 10 ml, and preferably between 10 and 50 ml, with respect to 1 g of an anhydrous tetomilast type B crystal.

The stirring temperature is not particularly limited. It is preferably between approximately 10° C. and 35° C., and more preferably between approximately 20° C. and 30° C. The stirring time is preferably between approximately 5 minutes and 3 hours, and more preferably between approximately 30 and 90 minutes.

In addition, when a tetomilast hydrate crystal is produced from an anhydrous tetomilast type B crystal, it is preferable to allow the tetomilast hydrate crystal produced by the aforementioned method separately to exist as a seed crystal in a suspension.

The time of adding a seed crystal is not particularly limited. It is preferable to add such a seed crystal before or during stirring.

The obtained tetomilast hydrate crystal can be separated by isolation operations such as filtration, concentration, or extraction. Moreover, after separation, the separated crystal may be subjected to a drying treatment by a known method. Furthermore, the crystal can be purified by a known purification operation.

The thus obtained tetomilast hydrate crystal has a purity of 95% or more, and it can be crushed using an ordinary crusher (for example, an atomizer).

Thus, a tetomilast crushed product having a mean particle size between 10 and 50 μm and a 90% cumulative particle size of 80 μm or smaller, which is suitable for formulation, can be obtained.

Anhydrous Tetomilast Type B Crystal

Figure 5:
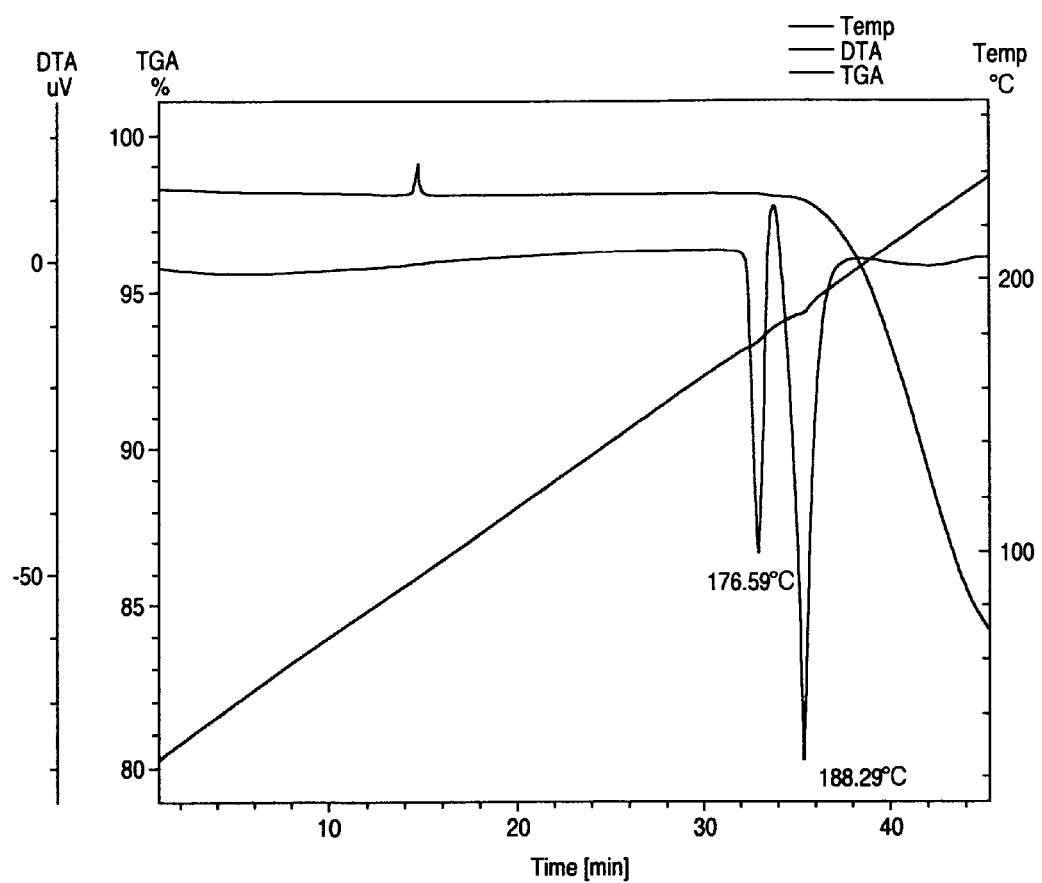
FIG. 5 is a view showing the thermogravimetry/differential thermal analysis of the anhydrous tetomilast type B crystal obtained in Reference example 1 (2)

An anhydrous tetomilast type B crystal has the physicochemical properties described in (4) to (6) below:

(4) The anhydrous tetomilast type B crystal has an endothermic curve that is substantially the same as the thermogravimetry/differential thermal analysis (temperature-rising rate/min) endothermic curve shown in FIG. 5. Specifically, such an anhydrous tetomilast type B crystal is characterized in that it has endothermic peaks around 177° C. and around 188° C.

Figure 6:
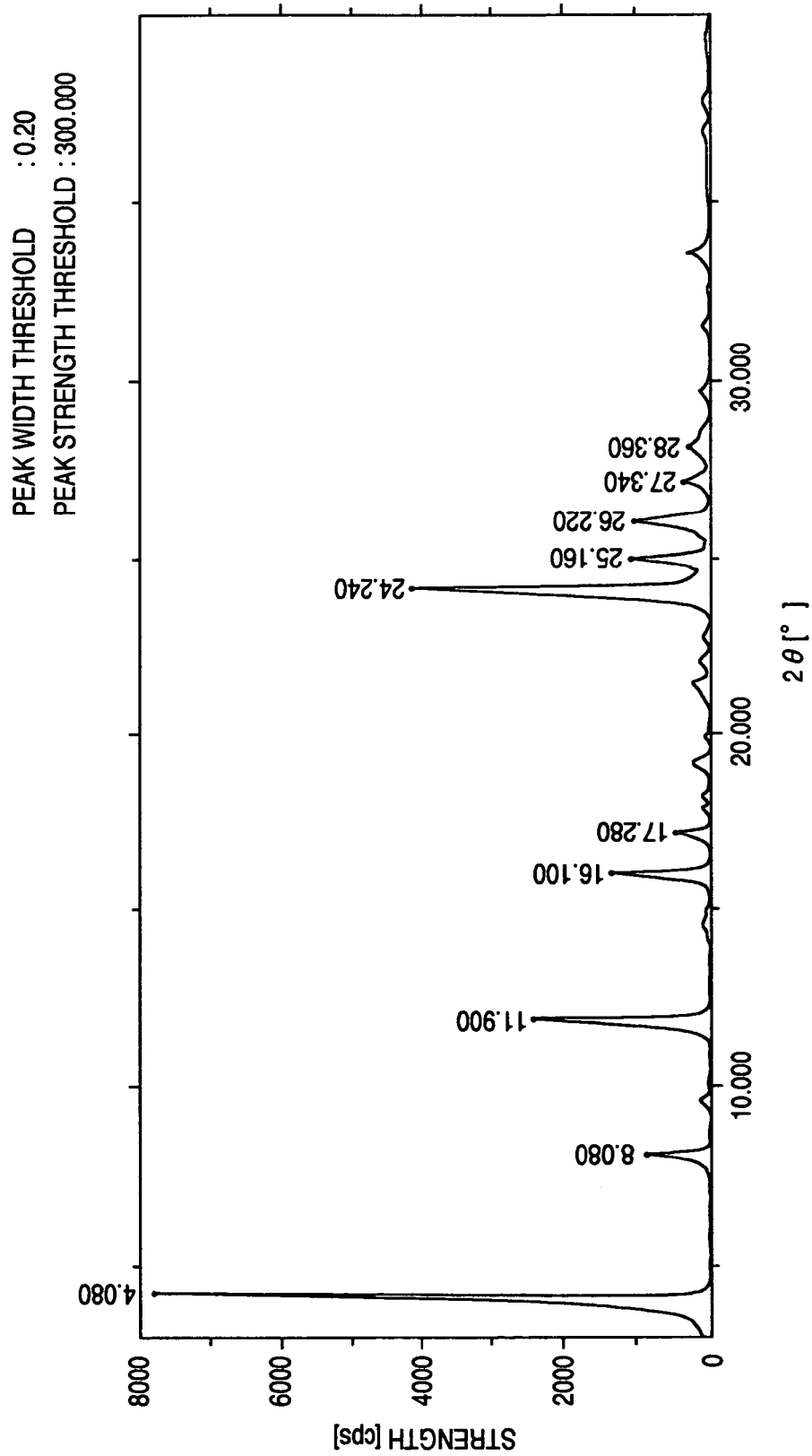
FIG. 6 is a view showing the powder X-ray diffraction of the anhydrous tetomilast type B crystal obtained in Reference example 1 (2)

(5) The anhydrous tetomilast type B crystal has a powder X-ray diffraction spectrum that is substantially the same as the powder X-ray diffraction spectrum shown in FIG. 6. Specifically, it has characteristic peaks at 2θ=4.1°, 8.1°, 11.9°, 16.1°, and 24.2°.

(6) The anhydrous tetomilast type B crystal has significant infrared absorption bands at 3298, 3090, 1744, 1593, 1474, 1348, 1269, 1132, 1045, 762, and 706 $cm^{-1}$ in the IR (KBr) spectrum.

The anhydrous tetomilast type B crystal can be produced by the method described in JP-A-5-51318 or Journal of Medicinal Chemistry, 1995, 38, pp. 353-358.

Moreover, the anhydrous tetomilast type B crystal may be obtained by completely dissolving a novel tetomilast crystal in a solvent while stirring under heating to reflux, and then allowing the obtained solution to stand to cool. Herein, such a novel tetomilast crystal can be used singly or as a mixture consisting of two or more types.

Examples of a solvent may include isopropanol, ethyl acetate, and a mixed solvent thereof.

The amount of a solvent used is not particularly limited, as long as it is able to completely dissolve a novel tetomilast crystal while stirring under heating to reflux. In the case of isopropanol, the amount used is preferably between 70 and 600 ml with respect to 1 g of a novel tetomilast crystal. In the case of ethyl acetate, it is preferably between 30 and 300 ml with respect to 1 g of a novel tetomilast crystal. When a mixed solvent consisting of isopropanol and ethyl acetate is used, isopropanol is mixed with ethyl acetate at any given ratio, and the amount of such a mixed solvent used may be adjusted so as to completely dissolve a novel tetomilast crystal while stirring under heating to reflux.

The obtained solution is cooled to approximately 30° C. over about 5 minutes to 1 hour, or is naturally cooled, so as to obtain an anhydrous tetomilast type B crystal. Further, after the suspension has been stood to cool, it may be cooled at a temperature of 10° C. or lower, and preferably at a temperature between approximately 0° C. and 10° C. By this operation, an anhydrous tetomilast type B crystal is obtained at a higher yield.

Furthermore, such an anhydrous tetomilast type B crystal is also obtained by allowing a basic compound to act on a novel tetomilast crystal so as to form salts, dissolving the salts in a suitable aqueous solvent, and then adding suitable acid to the obtained solution.

Examples of a basic compound may include carbonate, alkali metal hydroxide, and alkali earth metal hydroxide. Of these, alkali metal hydroxide is particularly preferable. Examples of carbonate may include sodium carbonate, potassium carbonate, sodium bicarbonate, and potassium bicarbonate. Examples of alkali metal hydroxide may include sodium hydroxide and potassium hydroxide. Examples of alkali earth metal hydroxide may include calcium hydroxide, barium hydroxide, and magnesium hydroxide. These compounds are used singly or as a mixture of two or more types. Of these, potassium hydroxide and sodium hydroxide are particularly preferable.

The additive amount of a basic compound is not particularly limited. It is generally 1 equivalent or greater, and preferably between approximately 1 and 1.5 equivalent, with respect to 1 equivalent of a novel tetomilast crystal to be treated.

Examples of the above described acid may include inorganic acids such as hydrochloric acid, sulfuric acid, and hydrobromic acid.

The additive amount of acid is generally 1 equivalent (neutralization amount) or greater, and preferably between approximately 1 and 1.5 equivalent, with respect to the above described basic compound used.

Examples of an aqueous solvent used herein may include those as described above in the method for producing a tetomilast hydrate crystal. Among others, acetone-water (an acetone content of 30% to 70% by volume) is particularly preferable.

The amount of an aqueous solvent used is not limited. It is 5 ml or greater, preferably between 5 and 300 ml, and more preferably between 30 and 70 ml, with respect to 1 g of a novel tetomilast crystal.

The temperature of a solution is preferably between 10° C. and 30° C. when acid is added.

A solution is converted to a suspension by addition of acid. Thus, such a suspension is cooled generally at 10° C. or lower, and preferably at a temperature between 0° C. and 10° C., so as to efficiently extract an anhydrous tetomilast type B crystal.

In addition, these methods are applied to anhydrous tetomilast type B crystals, so as to obtain anhydrous tetomilast type B crystals with higher purity.

Anhydrous Tetomilast Type A Crystal

Figure 3:
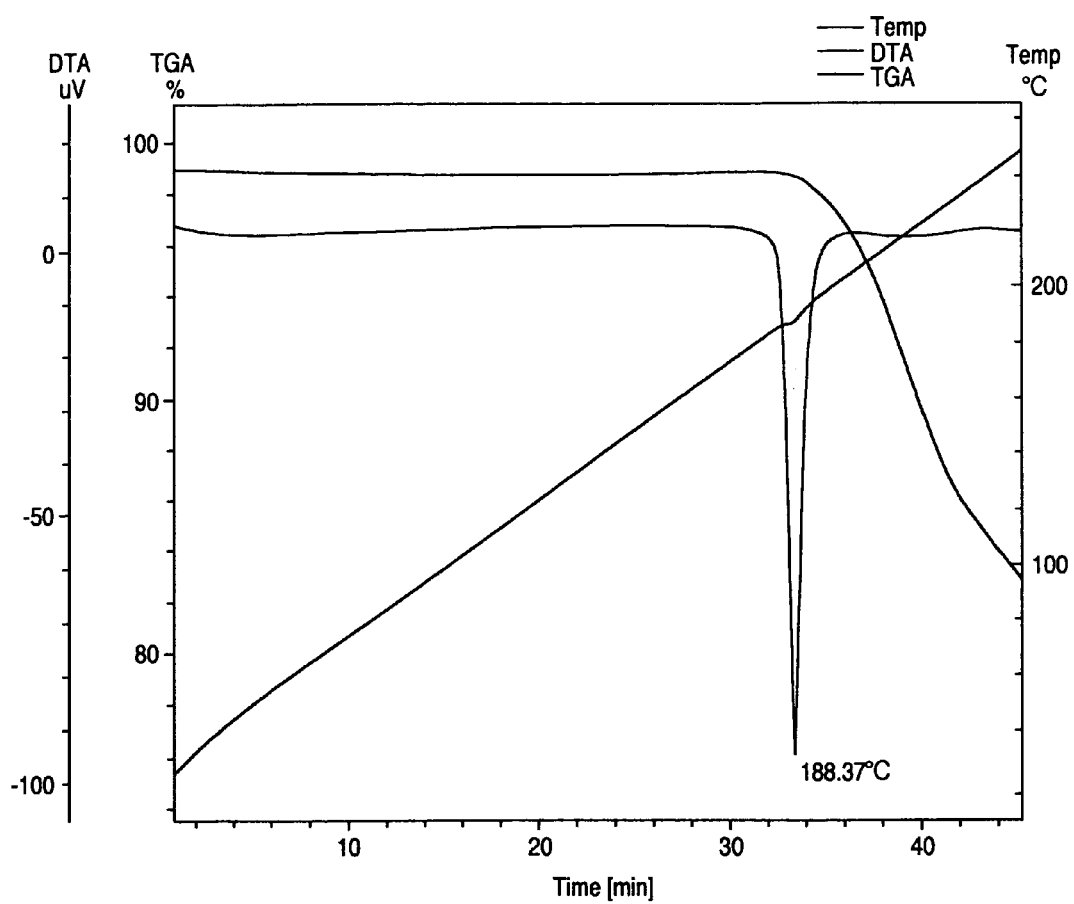
FIG. 3 is a view showing the thermogravimetry/differential thermal analysis of the anhydrous tetomilast type A crystal obtained in Example 1 (1)

An anhydrous tetomilast type A crystal has the physicochemical properties described in (7) to (9) below:

(7) The anhydrous tetomilast type A crystal has an endothermic curve that is substantially the same as the thermogravimetry/differential thermal analysis (temperature-rising rate/min) endothermic curve shown in FIG. 3. Specifically, such an anhydrous tetomilast type A crystal is characterized in that it has an endothermic peak around 188° C.

Figure 4:
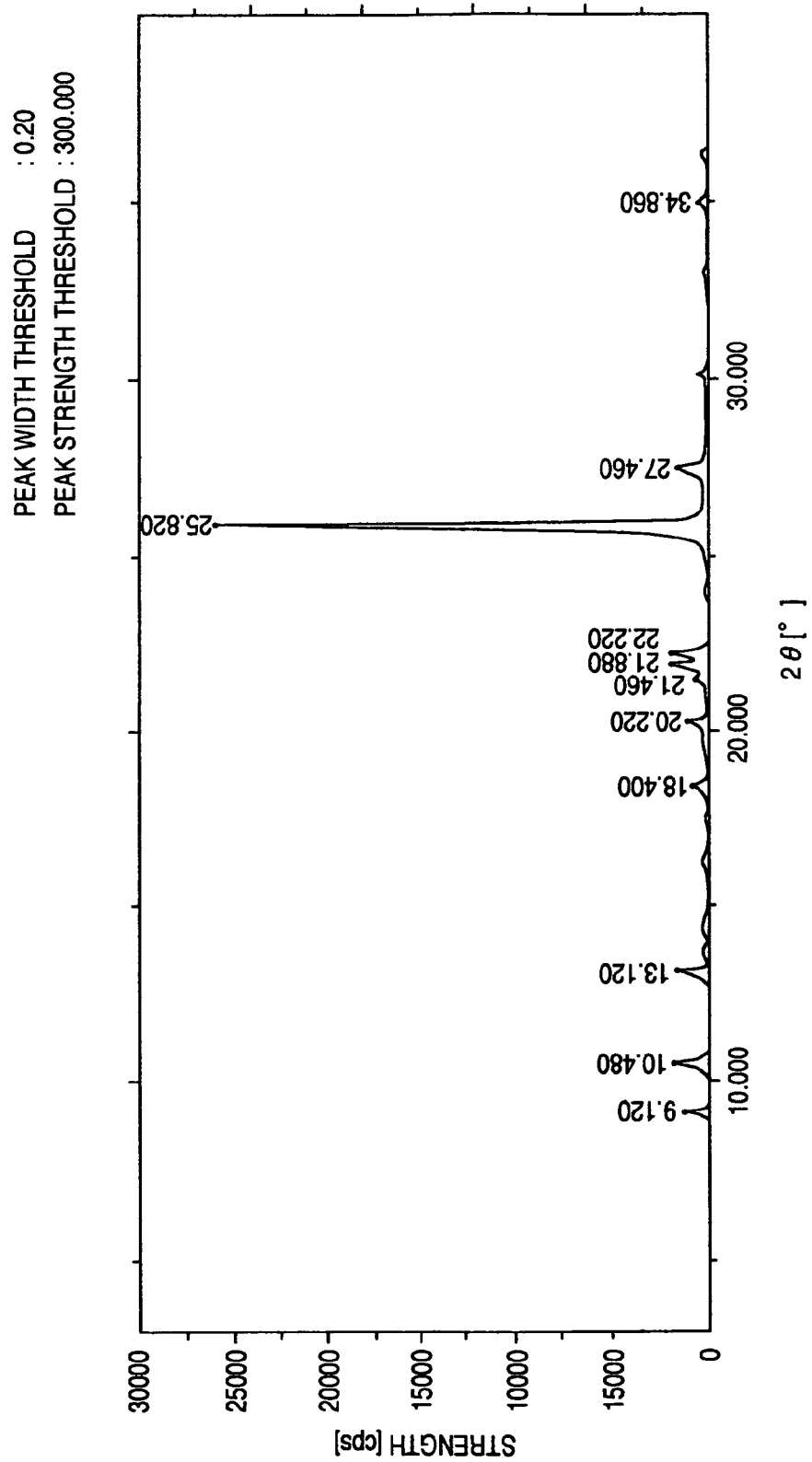
FIG. 4 is a view showing the powder X-ray diffraction of the anhydrous tetomilast type A crystal obtained in Example 1 (1)

(8) The anhydrous tetomilast type A crystal has a powder X-ray diffraction spectrum that is substantially the same as the powder X-ray diffraction spectrum shown in FIG. 4. Specifically, it has characteristic peaks at $2\theta=10.5°, 13.1°; 18.4°, 21.9°$, and $25.8°$.

(9) The anhydrous tetomilast type A crystal has significant infrared absorption bands at 3306, 3084, 1746, 1593, 1474, 1348, 1271, 1132, 1045, 758, and 704 $cm^{-1}$ in the IR (KBr) spectrum.

Method for Producing Anhydrous Tetomilast Type A Crystal

The anhydrous tetomilast type A crystal can be obtained by recrystallization from a solution that is obtained by dissolving a known anhydrous tetomilast type B crystal or an anhydrous tetomilast type B crystal obtained by the aforementioned method in a suitable solvent.

Examples of the aforementioned solvent that can be used herein may include ethanol, acetone, and acetone-water (an acetone content of 40% or more by volume). Of these, acetone-water (an acetone content of 40% or more by volume) is particularly preferable.

The amount of a solvent used is not particularly limited, as long as it is able to completely dissolve an anhydrous tetomilast type B crystal while stirring under heating to reflux. In the case of ethanol, the amount used is preferably between 70 and 400 ml with respect to 1 g of an anhydrous tetomilast type B crystal. In the case of acetone, it is preferably between 30 and 120 ml with respect to 1 g of the above anhydrous tetomilast type B crystal. In the case of acetone-water (an acetone content of 40% to 80% by volume), it is preferably between 30 and 500 ml with respect to 1 g of the above anhydrous tetomilast type B crystal.

Such an anhydrous tetomilast type B crystal is preferably dissolved in a solvent while stirring under heating to reflux. At that time, the heating temperature is not particularly limited. It is generally between approximately 40° C. and 85° C., and preferably between approximately 55° C. and 80° C.

After such dissolution, the temperature of the obtained solution is decreased, so that the anhydrous tetomilast type A crystal of the present invention can be crystallized.

The temperature-decreasing rate is not particularly limited. When ethanol is used as a solvent, for example, the temperature-decreasing rate is preferably 0.8° C./min or less. In addition, when acetone-water (an acetone content of 40% or more by volume) is used as a solvent, the temperature-decreasing rate is preferably 0.4° C./min or less. By setting the temperature-decreasing rate within such a range, the anhydrous tetomilast type A crystal of the present invention can be obtained more efficiently.

When acetone-water (an acetone content of 40% or more by volume) is used as a solvent, the aforementioned solution is retained at 40° C. to 50° C. for 60 minutes or longer, and it is then cooled, so that an anhydrous tetomilast type A crystal can be crystallized. The temperature-decreasing rate during the aforementioned cooling does not particularly affect crystallization of the anhydrous tetomilast type A crystal.

In addition, during such a decrease in the temperature, while the temperature is retained in several temperature ranges such as 40° C. to 50° C., 30° C. to 40° C., 15° C. to 25° C., or 0° C. to 10° C., the solution is stirred for approximately 30 minutes to 5 hours, so that the temperature may be decreased in a stepwise manner. In this stepwise temperature-decreasing method, at a temperature between 40° C. and 50° C., an anhydrous tetomilast type A crystal, which has been produced separately, may be added as a seed crystal.

Moreover, such an anhydrous tetomilast type A crystal is produced by using a novel tetomilast crystal (excluding an anhydrous tetomilast type A crystal) instead of the known anhydrous tetomilast type B crystal, and recrystallizing from a solution formed by dissolving the above novel tetomilast crystal in a suitable solvent.

Specifically, an anhydrous tetomilast type A crystal is produced by recrystallization from a solution formed by dissolving in a solvent at least one type of tetomilast crystal selected from the group consisting of a tetomilast hydrate crystal, an anhydrous tetomilast type C crystal, and a tetomilast acetonitrile solvate crystal.

Herein, a novel tetomilast crystal is used singly or as a mixture consisting of two or more types.

Such an anhydrous tetomilast type A crystal can also be produced by suspending the known anhydrous tetomilast type B crystal or a novel tetomilast crystal (excluding an anhydrous tetomilast type A crystal) in an aqueous solvent (a water content of 90% or less by volume), and then stirring the suspension.

Examples of an aqueous solvent that can be used herein may include mixed solvents formed by mixing organic solvents having high compatibility with water, such as methanol, ethanol, acetone, or tetrahydrofuran, with water.

Specifically, the aqueous solvent that can be used as a mixed solvent is consisting of water, and at least one organic solvent selected from the group consisting of methanol, ethanol, acetone, and tetrahydrofuran. In particular, acetone-water (an acetone content of 30% to 60% by volume) is preferable as such an aqueous solvent.

The temperature of a suspension is not particularly limited during stirring. It is generally between 0° C. and 65° C., and preferably between 10° C. and 60° C.

The stirring time is generally between 10 minutes and 48 hours, and preferably between 10 minutes and 3 hours.

In addition, these methods are applied to anhydrous tetomilast type A crystals, so as to obtain anhydrous tetomilast type A crystals with higher purity.

The obtained anhydrous tetomilast type A crystal can be separated by isolation operations such as filtration, concentration, or extraction. Moreover, after separation, the separated crystal may be subjected to a drying treatment by a known method. Furthermore, the crystal can be purified by a known purification operation.

The thus obtained anhydrous tetomilast type A crystal has a purity of 95% or more, and it can be crushed using an ordinary crusher (for example, an atomizer). Thus, a tetomilast crushed product having a mean particle size between 10 and 50 μm and a 90% cumulative particle size of 80 μm or smaller, which is suitable for formulation, can be obtained.

Anhydrous Tetomilast Type C Crystal

Figure 7:
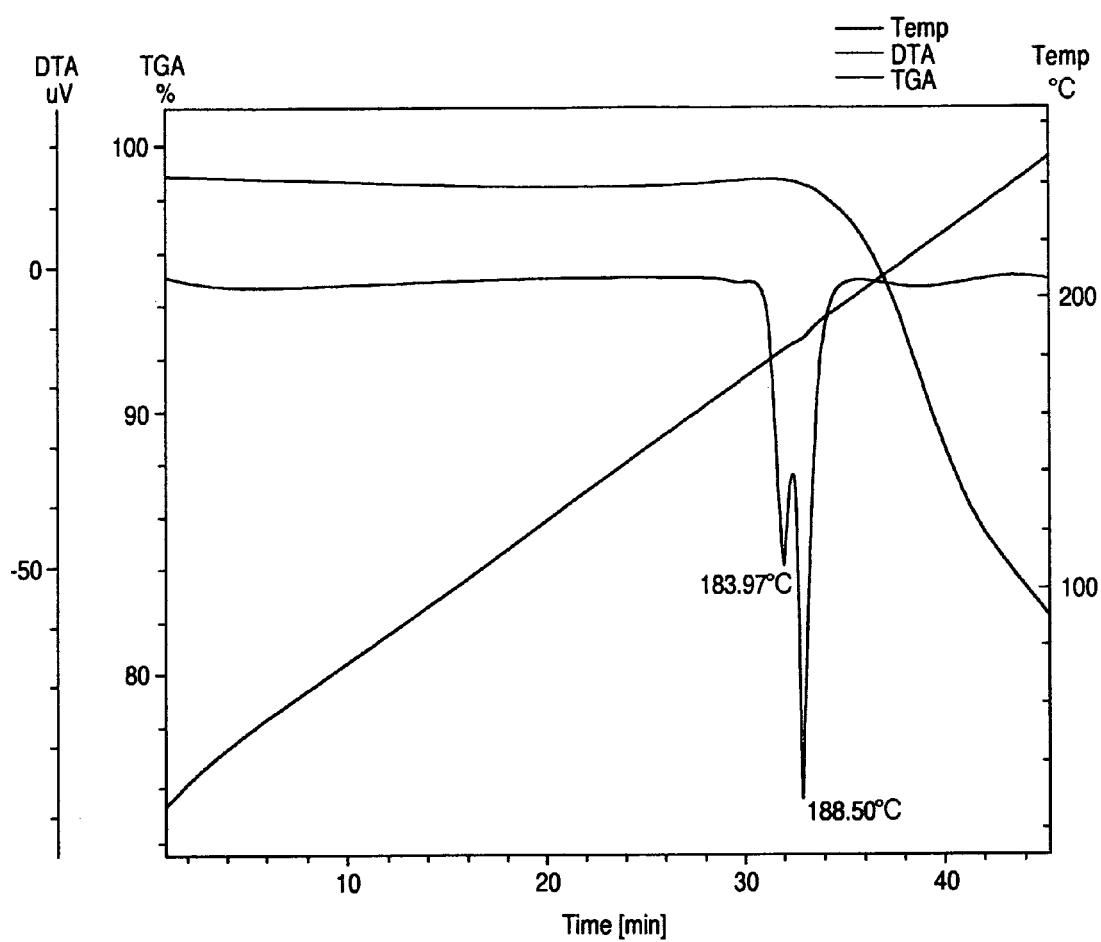
FIG. 7 is a view showing the thermogravimetry/differential thermal analysis of the anhydrous tetomilast type C crystal obtained in Example 2.

An anhydrous tetomilast type C crystal has the physicochemical properties described in (10) to (12) below:

(10) The anhydrous tetomilast type C crystal has an endothermic curve that is substantially the same as the thermogravimetry/differential thermal analysis (temperature-rising rate/min) endothermic curve shown in FIG. 7. Specifically, such an anhydrous tetomilast type C crystal is characterized in that it has endothermic peaks around 184° C. and around 189° C.

Figure 8:
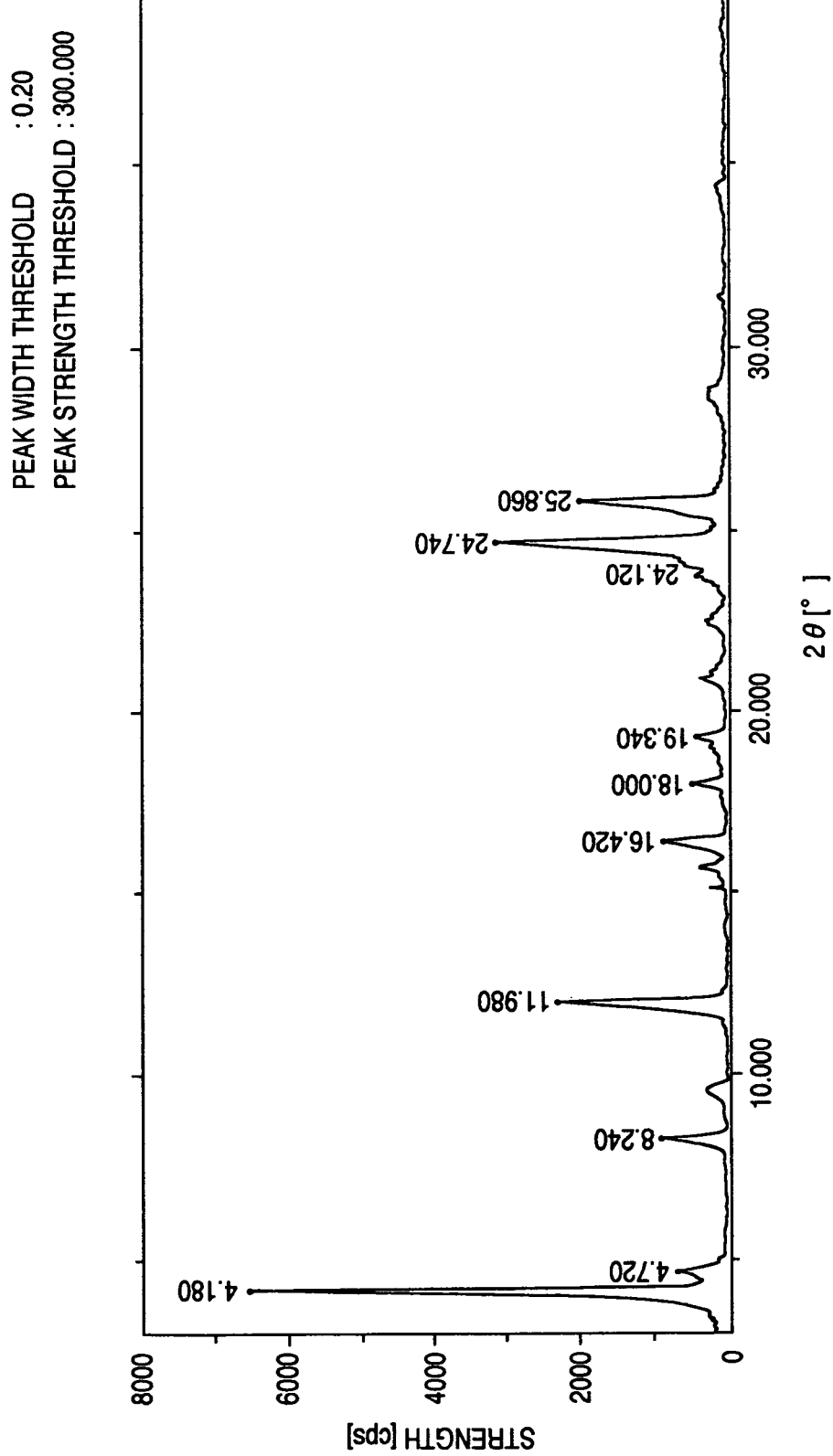
FIG. 8 is a view showing the powder X-ray diffraction of the anhydrous tetomilast type C crystal obtained in Example 2.

(11) The anhydrous tetomilast type C crystal has a powder X-ray diffraction spectrum that is substantially the same as the powder X-ray diffraction spectrum shown in FIG. 8. Specifically, it has characteristic peaks at 2θ=4.2°, 8.2°, 12.0°, 16.4°, 24.7°, and 25.9°.

(12) The anhydrous tetomilast type C crystal has significant infrared absorption bands at 3300, 3088, 1744, 1593, 1476, 1346, 1267, 1132, 1045, 754, and 704 $cm^{-1}$ in the IR (KBr) spectrum.

Method for Producing Anhydrous Tetomilast Type C Crystal

The anhydrous tetomilast type C crystal can be produced by recrystallization from a solution that is obtained by dissolving the known anhydrous tetomilast type B crystal or an anhydrous tetomilast type B crystal obtained by the aforementioned method in a suitable solvent.

Examples of a solvent that can be used herein may include methanol and ethanol. Of these, methanol is particularly preferable.

The amount of a solvent used is not particularly limited, as long as it is able to completely dissolve the aforementioned anhydrous tetomilast type B crystal while stirring under heating to reflux. The amount of a solvent used is preferably between 70 and 200 ml, and more preferably between 80 and 120 ml, with respect to 1 g of the aforementioned anhydrous tetomilast type B crystal.

After such dissolution, the temperature of the obtained solution is decreased to a temperature between 10° C. and 30° C., so that the anhydrous tetomilast type C crystal of the present invention can be crystallized. The temperature-decreasing rate is not particularly limited, when the solvent is methanol. It may be approximately 0.4° C. to 0.6° C./min. When ethanol is used as a solvent, the obtained solution may rapidly be cooled at a temperature-decreasing rate of 5° C./min or more, and preferably of 10° C./min or more. By setting the temperature-decreasing rate within such a range, the anhydrous tetomilast type C crystal of the present invention can be obtained more efficiently.

In addition, such an anhydrous tetomilast type C crystal is produced by recrystallization from a solution obtained by dissolving in a suitable solvent a novel tetomilast crystal (excluding the anhydrous tetomilast type C crystal) that is used instead of the known anhydrous tetomilast type B crystal.

Specifically, the known anhydrous tetomilast type B crystal is first added to methanol, and it is then dissolved therein while stirring under heating to reflux. The obtained solution is stood to cool to approximately 30° C. for about 40 minutes to 1 hour. Thereafter, the suspension obtained by the aforementioned cooling is cooled at 10° C. or lower, and preferably at a temperature between approximately 0° C. and 10° C., for 30 minutes to 3 hours, so that the anhydrous tetomilast type C crystal of the present invention can be obtained in the form of a crystal.

Specifically, an anhydrous tetomilast type C crystal is produced by recrystallization from a solution formed by dissolving in a solvent at least one type of tetomilast crystal selected from the group consisting of a tetomilast hydrate crystal, an anhydrous tetomilast type A crystal, and a tetomilast acetonitrile solvate crystal. Herein, a novel tetomilast crystal is used singly or as a mixture consisting of two or more types. The solvent and recrystallization conditions applied herein are equivalent to those in the case of using the aforementioned known anhydrous tetomilast type B crystal as a starting material.

Moreover, the aforementioned method is applied to anhydrous tetomilast type C crystals, so as to obtain anhydrous tetomilast type C crystals with higher purity.

The obtained anhydrous tetomilast type C crystal can be separated by isolation operations such as filtration, concentration, or extraction. Moreover, after separation, the separated crystal may be subjected to a drying treatment by a known method. Furthermore, the crystal can be purified by a known purification operation.

The thus obtained anhydrous tetomilast type C crystal has a purity of 95% or more, and it can be crushed using an ordinary Crusher (for example, an atomizer). Thus, a tetomilast crushed product having a mean particle size between 10 and 50 μm and a 90% cumulative particle size of 80 μm or smaller, which is suitable for formulation, can be obtained.

Tetomilast Acetonitrile Solvate Crystal

Figure 9:
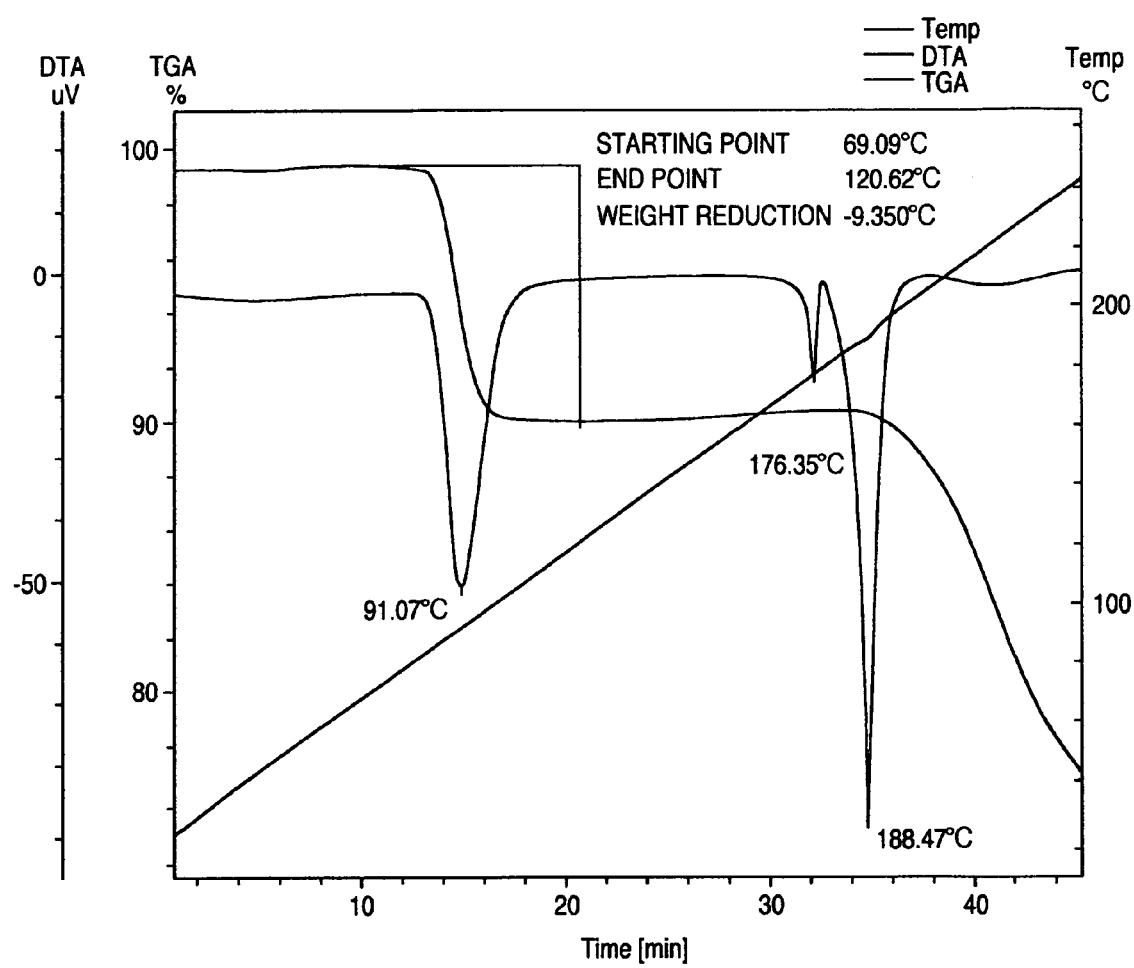
FIG. 9 is a view showing the thermogravimetry/differential thermal analysis of the tetomilast acetonitrile solvate crystal obtained in Example 3.

A tetomilast acetonitrile solvate crystal has the physicochemical properties described in (13) to (15) below:

(13) The tetomilast acetonitrile solvate crystal has an endothermic curve that is substantially the same as the thermogravimetry/differential thermal analysis (temperature-rising rate/min) endothermic curve shown in FIG. 9. Specifically, such a tetomilast acetonitrile solvate crystal is characterized in that it has endothermic peaks around 91° C., around 176° C., and around 189° C.

Figure 10:
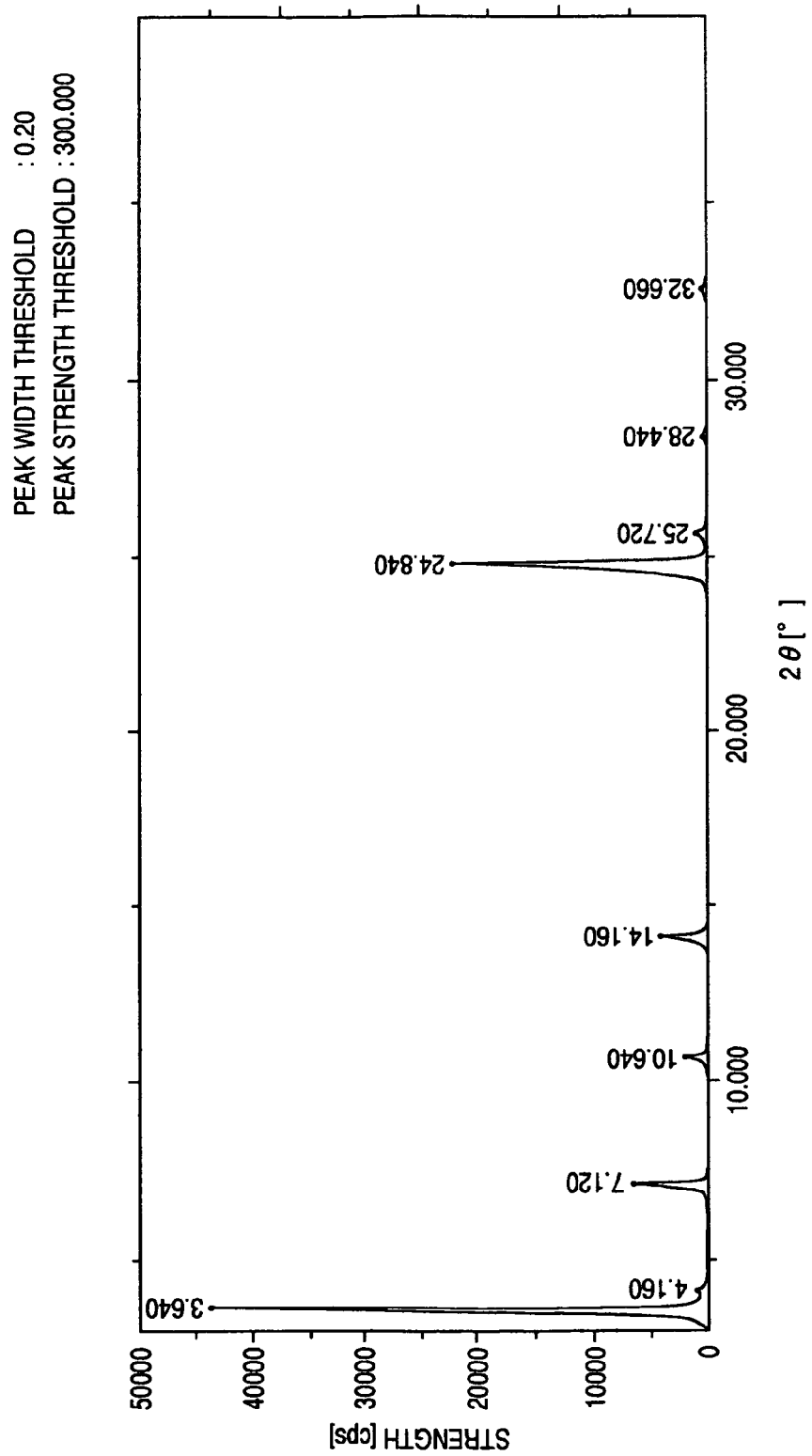
FIG. 10 is a view showing the powder X-ray diffraction of the tetomilast acetonitrile solvate crystal obtained in Example 3.

(14) The tetomilast acetonitrile solvate crystal has a powder X-ray diffraction spectrum that is substantially the same as the powder X-ray diffraction spectrum shown in FIG. 10. Specifically, it has characteristic peaks at 2θ=3.6°, 7.1°, 10.6°, 14.2°, and 24.8°.

(15) The tetomilast acetonitrile solvate crystal has significant infrared absorption bands at 3300, 3090, 2249 (nitrile group), 1744, 1593, 1476, 1346, 1269, 1132, 1045, 752, and 704 $cm^{-1}$ in the IR (KBr) spectrum.

Method for Producing Tetomilast Acetonitrile Solvate Crystal

The tetomilast acetonitrile solvate crystal can be produced by recrystallization from a solution that is obtained by dissolving in acetonitrile the known anhydrous tetomilast type B crystal or an anhydrous tetomilast type B crystal obtained by the aforementioned method.

The amount of acetonitrile used is not particularly limited, as long as it is able to completely dissolve the above anhydrous tetomilast type B crystal while stirring under heating to reflux. The amount of acetonitrile used is preferably between 70 and 150 ml, and more preferably between 70 and 100 ml, with respect to 1 g of the above anhydrous tetomilast type B crystal.

The above anhydrous tetomilast type B crystal may be dissolved in acetonitrile while stirring under heating to reflux, for example. After such dissolution, the temperature of the solution in which the anhydrous tetomilast type B crystal has been dissolved is decreased, so that the tetomilast acetonitrile solvate crystal of the present invention can be crystallized. The temperature-decreasing rate is not particularly limited, and it may be between approximately 0.1° C./min and 1.5° C./min. The tetomilast acetonitrile solvate crystal of the present invention is not particularly affected by such a temperature-decreasing rate, and it can preferably be obtained.

Specifically, the known anhydrous tetomilast type B crystal is added to acetonitrile, and it is then dissolved therein while stirring under heating to reflux. The obtained solution is stood to cool to approximately 30° C. for about 30 minutes to 8 hours. Thereafter, the suspension obtained by the aforementioned cooling is cooled at 10° C. or lower, and preferably at a temperature between approximately 0° C. and 10° C., for 30 minutes to 3 hours, so that the tetomilast acetonitrile solvate crystal of the present invention can be obtained in the form of a crystal.

In addition, such a tetomilast acetonitrile solvate crystal is produced by recrystallization from a solution obtained by dissolving in acetonitrile a novel tetomilast crystal (excluding the tetomilast acetonitrile solvate crystal) that is used instead of the known anhydrous tetomilast type B crystal.

Specifically, an tetomilast acetonitrile solvate crystal is produced by recrystallization from a solution formed by dissolving in acetonitrile at least one type of tetomilast crystal selected from the group consisting of a tetomilast hydrate crystal, an anhydrous tetomilast type A, and an anhydrous tetomilast type C crystal. Herein, a novel tetomilast crystal is used singly or as a mixture consisting of two or more types. The solvent and recrystallization conditions applied herein are equivalent to those in the case of using the aforementioned known anhydrous tetomilast type B crystal as a starting material.

Moreover, the aforementioned method is applied to tetomilast acetonitrile solvate crystals, so as to obtain tetomilast acetonitrile solvate crystals with higher purity.

The obtained tetomilast acetonitrile solvate crystal can be separated by isolation operations such as filtration, concentration, or extraction. Moreover, after separation, the separated crystal may be subjected to a drying treatment by a known method. Furthermore, the crystal can be purified by a known purification operation.

The thus obtained tetomilast acetonitrile solvate crystal has a purity of 95% or more, and it can be crushed using an ordinary crusher (for example, an atomizer). Thus, a tetomilast crushed product having a mean particle size between 10 and 50 μm and a 90% cumulative particle size of 80 μm or smaller, which is suitable for formulation, can be obtained.

Figure 11:
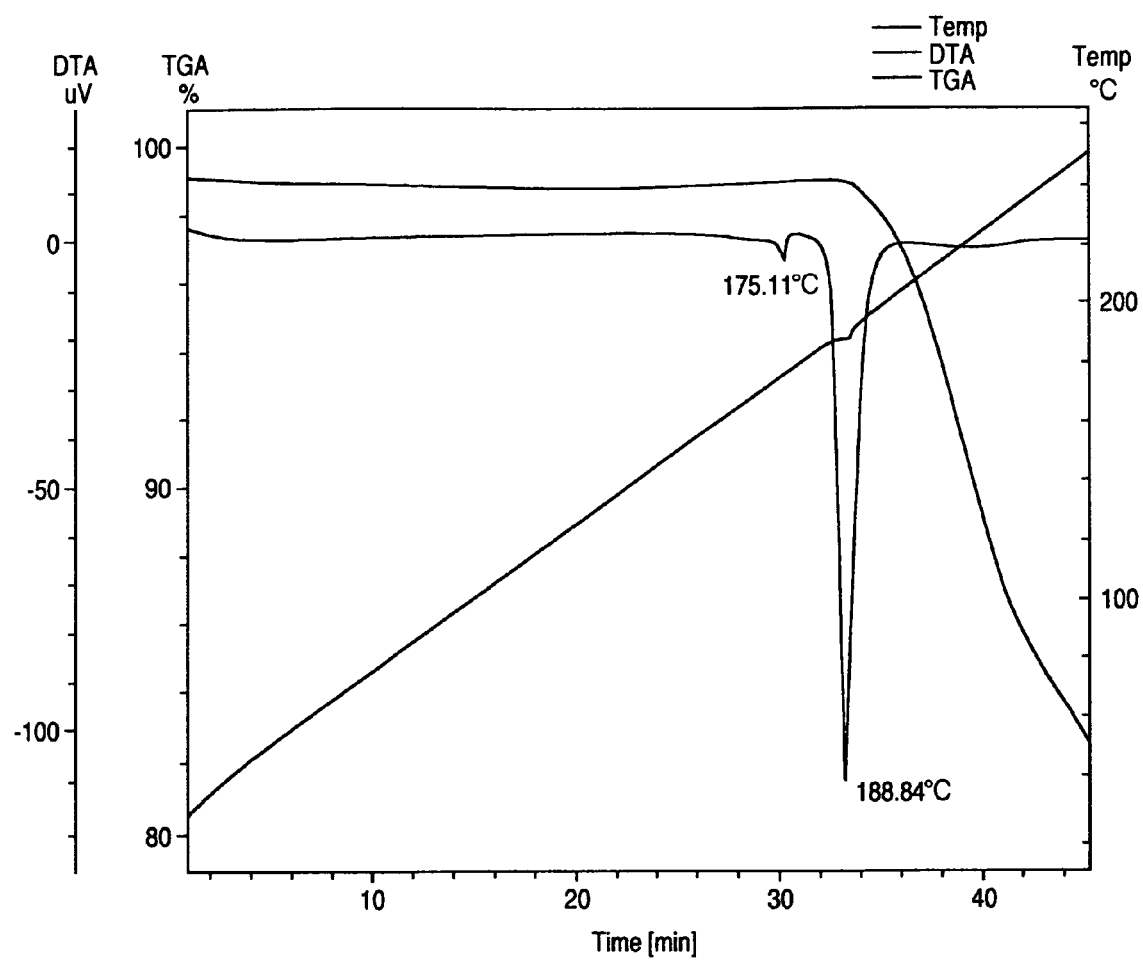
FIG. 11 is a view showing the thermogravimetry/differential thermal analysis of the mixture consisting of an anhydrous tetomilast type A crystal and an anhydrous tetomilast type B crystal obtained in Example 4(1)

Mixture Consisting of Anhydrous Tetomilast Type A Crystal and Anhydrous Tetomilast Type B Crystal As a mixture consisting of an anhydrous tetomilast type A crystal and an anhydrous tetomilast type B crystal, mixtures with various types of ratios are generated depending on production conditions. As an example, a mixture having the physicochemical properties described in (16) to (18) below can be generated:

(16) The level of an endothermic peak depends on the mixing ratio of type A crystals and type B crystals. FIG. 11 shows the endothermic peak of a sample having a mixing ratio of A:B=40:60. The mixture consisting of an anhydrous tetomilast type A crystal and an anhydrous tetomilast type B crystal has an endothermic curve that is substantially the same as the thermogravimetry/differential thermal analysis (temperature-rising rate/min) endothermic curve shown in FIG. 11. Specifically, such a mixture is characterized in that it has endothermic peaks around 175° C. and around 189° C.

Figure 12:
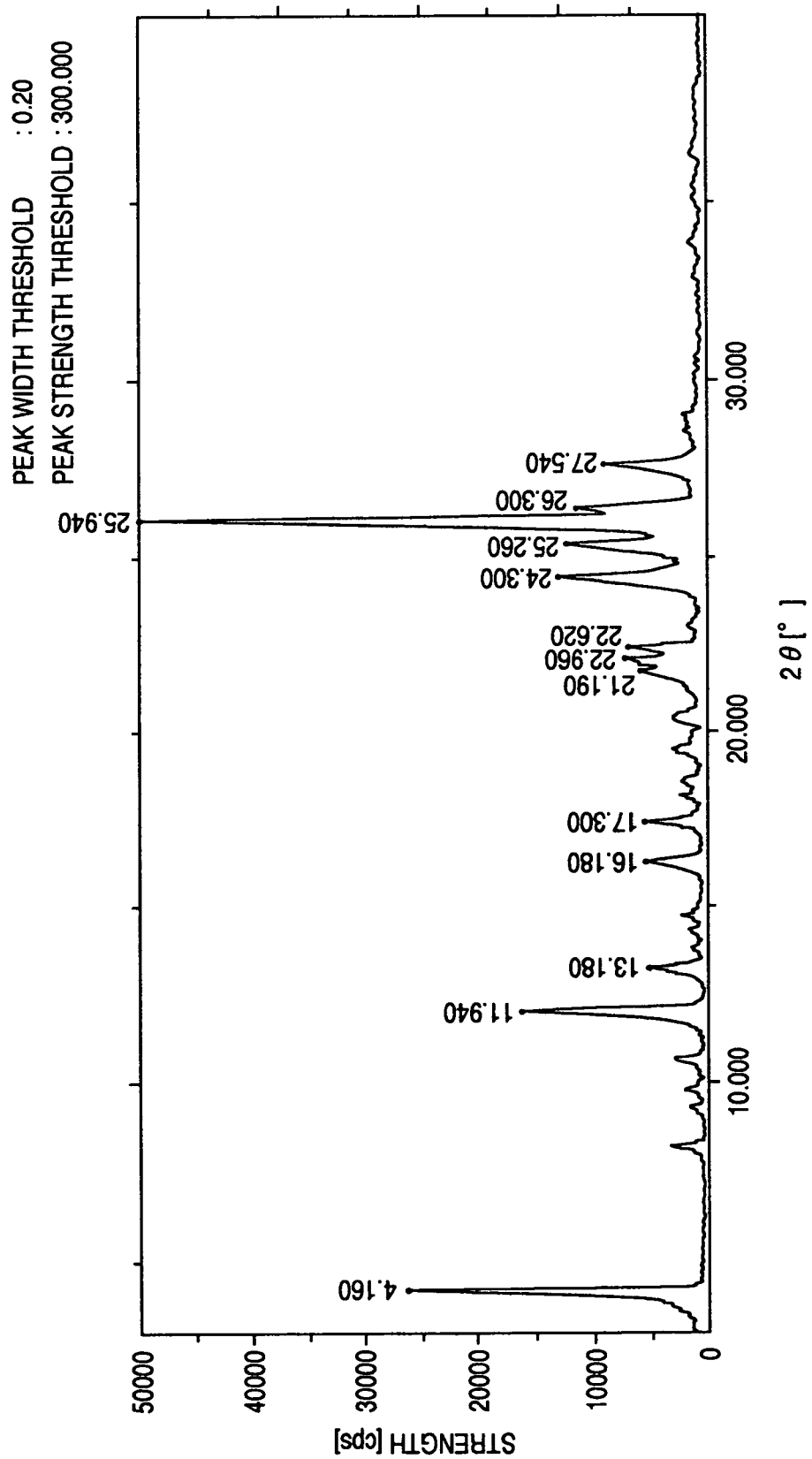
FIG. 12 is a view showing the powder X-ray diffraction of the mixture consisting of an anhydrous tetomilast type A crystal and an anhydrous tetomilast type B crystal obtained in Example 4(1)

(17) The powder X-ray diffraction spectrum of the mixture consisting of an anhydrous tetomilast type A crystal and an anhydrous tetomilast type B crystal is the sum of the powder X-ray diffraction spectrum of a pure anhydrous tetomilast type A crystal and the powder X-ray diffraction spectrum of a pure anhydrous tetomilast type B crystal. The strength of a peak derived from each crystal form is affected by the mixing ratio between the anhydrous tetomilast type A crystal and the anhydrous tetomilast type B crystal. FIG. 12 shows the powder X-ray diffraction spectrum of a sample having a mixing ratio of the anhydrous tetomilast type A crystal: the anhydrous tetomilast type B crystal=40:60.

(18) The sample having a mixing ratio of the anhydrous tetomilast type A crystal: the anhydrous tetomilast type B crystal=40:60 has significant infrared absorption bands at 3298, 3088, 1744, 1593, 1474, 1348, 1269, 1132, 1045, 760, and 704 $cm^{-1}$ in the IR (KBr) spectrum. In addition, a deviation of $\pm 5$ $cm^{-1}$ may be generated in an absorption peak due to a difference in the mixing ratio between the anhydrous tetomilast type A crystal and the anhydrous tetomilast type B crystal.

Figure 13:
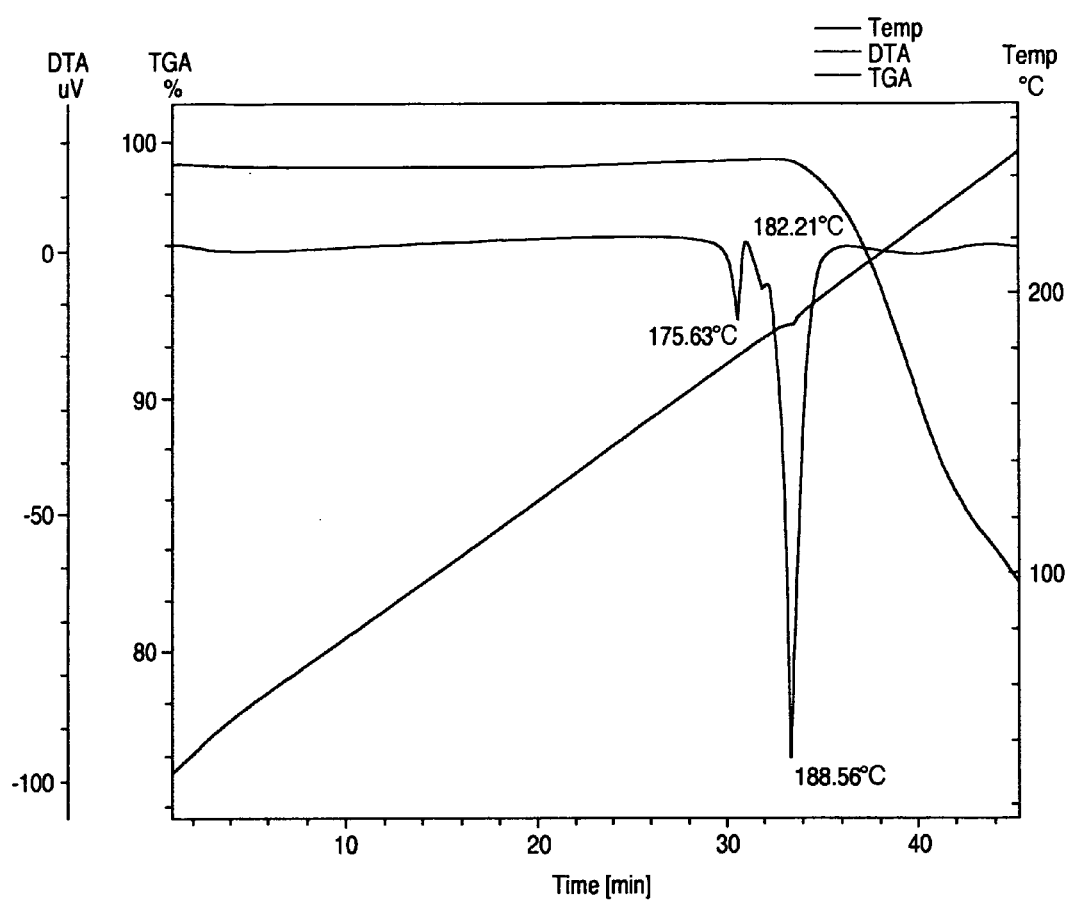
FIG. 13 is a view showing the thermogravimetry/differential thermal analysis of the mixture consisting of an anhydrous tetomilast type A crystal and an anhydrous tetomilast type B crystal obtained in Example 4(2)

Moreover, a sample having a mixing ratio of A:B=10:90 has the physicochemical properties described in (19) to (21) below:

(19) The sample has an endothermic curve that is substantially the same as the thermogravimetry/differential thermal analysis (temperature-rising rate/min) endothermic curve shown in FIG. 13. Specifically, such a sample is characterized in that it has endothermic peaks around 176° C. and around 189° C.

Figure 14:
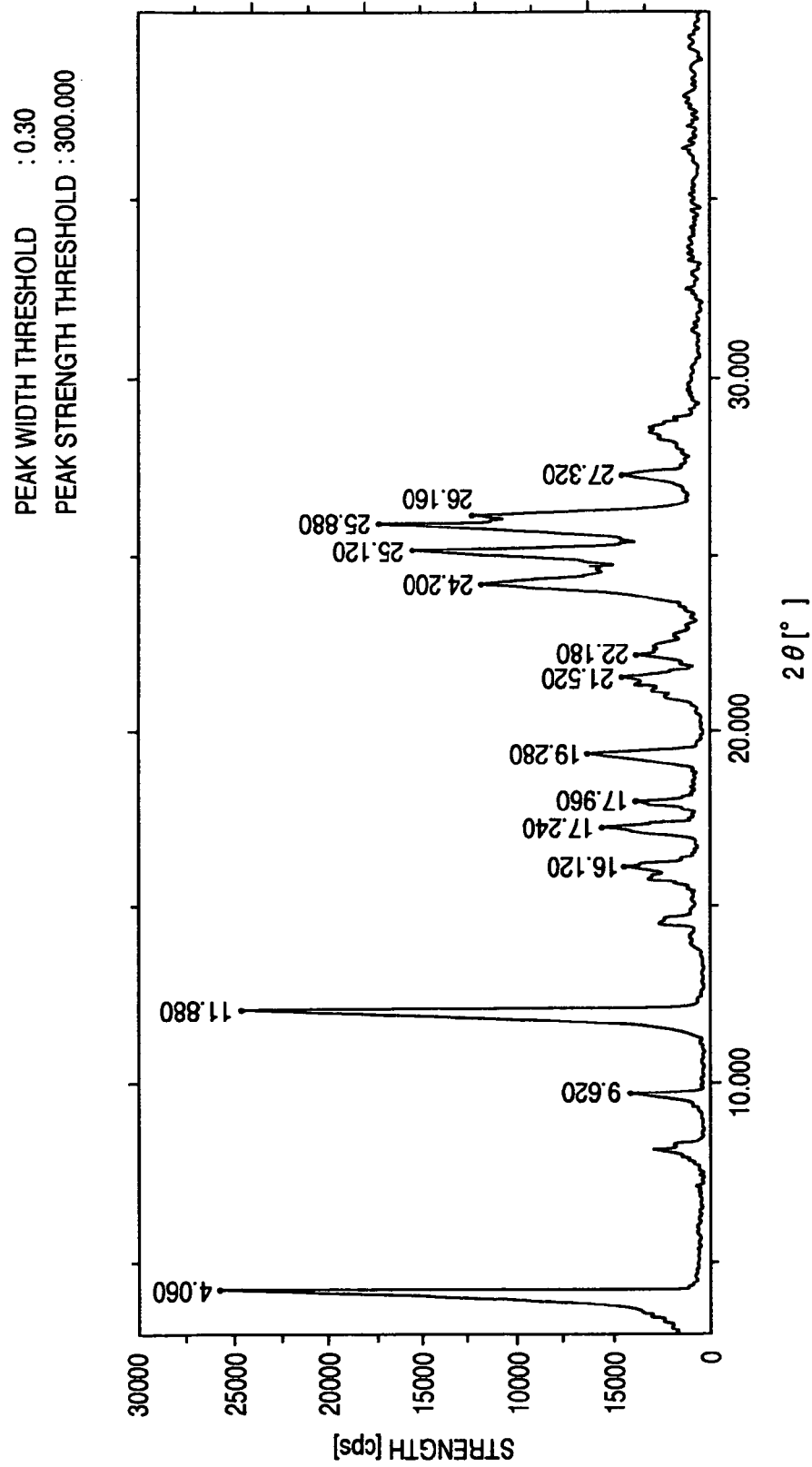
FIG. 14 is a view showing the powder X-ray diffraction of the mixture consisting of an anhydrous tetomilast type A crystal and an anhydrous tetomilast type B crystal obtained in Example 4 (2).

(20) The sample has a powder X-ray diffraction spectrum that is substantially the same as the powder X-ray diffraction spectrum shown in FIG. 14. Specifically, it has characteristic peaks at 2θ=4.1°, 11.9°, 16.1°, 17.2°, 19.3°, 24.2°, 25.1°, 25.9°, and 27.3°.

(21) The sample has significant infrared absorption bands at 3298, 3090, 1744, 1593, 1474, 1348, 1269, 1132, 1045, 756, and 706 $cm^{-1}$ in the IR (KBr) spectrum.

Method for Producing Mixture Consisting of Anhydrous Tetomilast Type A Crystal and Anhydrous Tetomilast Type B Crystal A mixture consisting of an anhydrous tetomilast type A crystal and an anhydrous tetomilast type B crystal can be produced by recrystallization from a solution that is obtained by dissolving in a suitable solvent the known anhydrous tetomilast type B crystal or an anhydrous tetomilast type B crystal obtained by the aforementioned method.

The type of the aforementioned solvent is not particularly limited. Acetone-water (an acetone content of 40% to 95% by volume) is preferable.

The amount of the aforementioned solvent used is not particularly limited, as long as it is able to completely dissolve the above tetomilast crystal while stirring under heating to reflux. The amount of the solvent used is preferably between 30 and 160 ml, and more preferably between 30 and 50 ml, with respect to 1 g of the above anhydrous tetomilast type B crystal.

The above tetomilast crystal may be dissolved in the aforementioned solvent while stirring under heating to reflux, for example. After such dissolution, the temperature of the solution in which the anhydrous tetomilast type B crystal has been dissolved is decreased, so that the mixture consisting of, an anhydrous tetomilast type A crystal and an anhydrous tetomilast type B crystal of the present invention can be obtained. The temperature-decreasing rate may be between approximately 0.4° C./min and 1.9° C./min. In particular, the temperature-decreasing rate is adjusted, so as to control the mixing ratio of the mixture consisting of an anhydrous tetomilast type A crystal and an anhydrous tetomilast type B crystal of the present invention.

Specifically, the anhydrous tetomilast type B crystal is first added to acetone-water (an acetone content of 40% to 95% by volume), and it is then dissolved therein while stirring under heating to reflux (approximately 60° C.). The obtained solution is stood to cool to approximately 30° C. for about 15 minutes to 1 hour. Thereafter, the suspension obtained by the aforementioned cooling is cooled at 10° C. or lower, and preferably at a temperature between approximately 0° C. and 10° C., for 30 minutes to 3 hours, so that the mixture consisting of an anhydrous tetomilast type A crystal and an anhydrous tetomilast type B crystal of the present invention can be obtained in the form of a crystal. In a case where the solution obtained after stirring under heating to reflux is quenched (for example, the solution is cooled to 10° C. or lower, and preferably to a temperature between approximately 0° C. and 10° C., for about 5 minutes to 1 hour), a mixture having a ratio of the anhydrous tetomilast type A crystal: the anhydrous tetomilast type B crystal=approximately 10:90 (weight ratio) can be obtained.

The ratio of the mixture consisting of the anhydrous tetomilast type A crystal and the anhydrous tetomilast type B crystal is not particularly limited.

In addition, the aforementioned mixture can also be produced using a novel tetomilast crystal (excluding the mixture consisting of an anhydrous tetomilast type A crystal and an anhydrous tetomilast type B crystal) instead of the known anhydrous tetomilast type B crystal. Specifically, the aforementioned mixture is produced by recrystallization from a solution formed by dissolving in a solvent at least one type of tetomilast crystal selected from the group consisting of a tetomilast hydrate crystal, an anhydrous tetomilast type A crystal, an anhydrous tetomilast type C crystal, and a tetomilast acetonitrile solvate crystal.
The solvent and recrystallization conditions applied herein are equivalent to those in the case of using the aforementioned known anhydrous tetomilast type B crystal as a starting material.

The obtained mixture consisting of an anhydrous tetomilast type A crystal and an anhydrous tetomilast type B crystal can be separated by isolation operations such as filtration, concentration, or extraction. Moreover, after separation, the separated crystal may be subjected to a drying treatment by a known method. Furthermore, the crystal can be purified by a known purification operation.

The thus obtained mixture consisting of an anhydrous tetomilast type A crystal and an anhydrous tetomilast type B crystal has a purity (the content ratio of the anhydrous tetomilast type A crystal and the anhydrous tetomilast type B crystal to the total content) of 95% or more, and it can be crushed using an ordinary crusher (for example, an atomizer). Thus, a tetomilast crushed product having a mean particle size between 10 and 50 μm and a 90% cumulative particle size of 80 μm or smaller, which is suitable for formulation, can be obtained.

Pharmaceutical Composition

The pharmaceutical composition of the present invention comprises at least one type of tetomilast crystal selected from the group consisting of a tetomilast hydrate crystal, an anhydrous tetomilast type A crystal, an anhydrous tetomilast type C crystal, and a tetomilast acetonitrile solvate crystal.

The pharmaceutical composition of the present invention further comprises an anhydrous tetomilast type B crystal. An example of such a pharmaceutical composition comprises a mixture consisting of an anhydrous tetomilast type A crystal and an anhydrous tetomilast type B crystal.

The novel tetomilast crystal of the present invention has activity of suppressing the release of active oxygen from neutrophils, or of eliminating reactive oxygen species. Thus, the above novel tetomilast crystal has action to prevent generation of peroxide lipid in a living body, or to decrease such generation. Accordingly, the novel tetomilast crystal of the present invention is useful as an agent for preventing and/or treating various types of disorders or diseases that are caused by the aforementioned excessive generation of reactive oxygen species, accumulation of peroxide lipid in a living body, or a defect in defense mechanism towards these phenomena. More specifically, an agent comprising the pharmaceutical composition of the present invention is useful, in a pharmaceutical field, as an agent for protecting various types of tissue cells from ischemia and disorders associated with revascularization, such as an agent for preventing and/or treating gastrointestinal ulcer including stress ulcer; an agent for preventing and/or treating cardiac ischemic diseases such as myocardial infarct or arrhythmia; an agent for preventing and/or treating cerebrovascular diseases such as cerebral hemorrhage, cerebral infarct, or transient ischemic attack; a liver and kidney function improver used for disorders caused by transplantation, microcirculation failure, etc.; or an agent for suppressing various types of cell injury that seem to be caused by active oxygen that is abnormally generated due to causes other than ischemia, such as an agent for preventing and/or treating Behcet's disease, cutaneous vasculitis, ulcerative colitis, malignant rheumatism, arthritis, arteriosclerosis or diabetes.

Moreover, the novel tetomilast crystal of the present invention is effective for various types of diseases associated with abnormal generation of cytokines, and particularly, abnormal generation of TNF-α, IL-β, IL-6, IFN-γ, etc., or various types of diseases associated with an acceleration state of adhesive action. In particular, the novel tetomilast crystal of the present invention can preferably be used: as an agent for preventing and/or treating various diseases such as chronic rheumatoid arthritis, endotoxin shock, ARDS caused by accidental ingestion of gastric juice, toxic gas, or septicemia, thermal burn or asthma, or myocardial infarction that is a myocardial ischemic state, viral myocarditis such as the acute stage of viral myocarditis, chronic heart failure such as ischemic myocardosis, spontaneous dilated cardiomyopathy, etc.; and as an agent for preventing and/or treating ischemic reperfusion abnormality occurring during coronary-artery bypass surgery (CABG) or during the use of artificial heart and lung, transition from SIRS (systemic inflammatory response syndrome) to organ failure (grave acute pancreatitis, DIC, etc.), or multiple organ failure caused by grave acute pancreatitis, liver failure occurring after hepatectomy for liver cancer, etc.; inflammatory bowel diseases such as Crohn's disease, ulcerative colitis, etc.; a series of autoimmune diseases such as hypergammaglobulinemia, systemic erythematodes (SLE) or multiple sclerosis, metastasis, immunological rejection occurring during transplantation, monoclonal B cell abnormality (myeloma, etc.), polyclonal B cell abnormality, atrial myxoma, Castleman's syndrome, primary glomerulonephritis, mesangial proliferative nephritis, cancer cachexia, Lennert's lymphoma, psoriasis, atopic dermatitis, Kaposi's sarcoma developed due to AIDS, postmenopausal osteoporosis, diabetes, septicemia, arteriosclerosis, or inflammatory diseases such as angitis or hepatitis or an agent for preventing and/or treating chronic obstructive pulmonary disease.

Specifically, the novel tetomilast crystal of the present invention has action to improve a decrease in lung functions, such as airflow obstruction, and it exhibits an extremely high therapeutic effect upon chronic obstructive pulmonary disease.

The tetomilast crystals of the present invention can be used with at least one of the members selected from the group consisting of:

1. leukotriene biosynthesis inhibitors (5-lipoxygenase inhibitors and a 5-lipoxygenase activating protein (FLAP) antagonists);
2. receptor antagonists for leukotrienes LTB4, LTC4, FTD4 or LTE4;
3. PDE4 inhibitors including inhibitors of isoform PDE4D;
4. 5-lipoxygenase inhibitors and a 5-lipoxygenase activating protein (FLAP) antagonists;
5. dual inhibitors of 5-lipoxygenase and antagonists of platelet activating factor (PAF);
6. leukotriene antagonists (LTRAs) including those for LTB4, LTC4, LTD4 and LTE4;
7. Antihistaminic H1 receptor antagonists;
8. H2 receptor antagonists;
9. α1 and α2 adrenoceptor agonist vasoconstrictor sympathomimetic agents administered orally or topically for decongestant use;
10. α1 and α2 adrenoceptor agonists in combination with inhibitors of 5-lipoxygenase;
11. anticholinergic agents;
12. β1- to β4-adrenoceptor agonists;
13. methylxanthines;
14. sodium cromoglicate;
15. muscarinic receptor (M1, M2 and M3) antagonists;
16. NSAIDs (Non-steroid anti-inflammatory drugs) including COX-1 inhibitors, COX-2 selective inhibitors, and nitric monoxide;
17. insulin like growth factor-1 (IGF-1) and its mimetics;
18. ciclesonide,
19. inhaled glucocorticoids (of which side effects are reduced);
20. tryptase inhibitors;
21. platelet activating factor antagonists;
22. monoclonal antibodies active against endogenous inflammatory entities;
23. IPL576;
24. antitumor nucrosis factor (TNF-α) agents;
25. DMARD (including leflunomide);
26. TCR peptides;
27. interleukin converting enzyme (ICE) inhibitors;
28. IMPDH inhibitors;
29. adhesion molecule inhibitors including a VLA-4 antagonists;
30. cathepsins;
31. MAP kinase inhibitors;
32. glucose-6-phosphate dehydrogenase inhibitors;
33. kinin-B1 or kinin-B2 receptor antagonists;
34. gold in the form of an aurothio group in combination with hydrophilic groups;
35. immunosuppressive agents;
36. antigout agents;
37. xanthine oxidaze inhibitors;
38. uricosuric agents;
39. antitumor agents;
40 growth hormone secretagogues;
41. MMP (matrix metalloproteases) inhibitors;
42. TGF-β (transforming growth factor);
43. PDGF (platelet-derived growth factor);
44. fibroblast growth factor (for example, basic fibroblast growth factor: b-FGF);
45. granulocyte-macrophage colony stimulating factor (GM-CSF);
46. capsaicin cream;
47. tachykinin NK1 and NK3 receptor antagonists;
48. elastase inhibitors;
49. PDE3 inhibitors;
50. H4 receptor antagonist or a inverse agonists;
51. antioxidant agens;
52. radical scavenging agents;
53. combinations of β2 adrenoceptor agonists and glucocorticoids;
54. agents increasing protein level of hypoxia-inducible factor-1α (HIF-1α);
55. antioxidant proteins upregulated by HIF-1α;
56. vascular endothelial growth factor (VEGF) secretagogus; and
57. VEGF receptor agonists.

The novel tetomilast crystal of the present invention is generally used in the form of a common pharmaceutical preparation. Such a pharmaceutical preparation is prepared using commonly used diluents or excipients such as a filler, an extender, a binder, a wetting agent, a disintegrator, a surfactant, or a lubricant. For such a pharmaceutical preparation, various types of forms can be selected depending on therapeutic purpose. Typical forms of such a pharmaceutical preparation may include a tablet, a pill, a powder, solution, suspension, emulsion, a granule, a capsule, a suppository, and an injection (solution, suspension, etc.). When the present tetomilast crystal is molded into the form of a tablet, various types of carriers, which have previously been known in the present field, can widely be used. Examples of such a carrier that can be used herein may include: excipients such as lactose, saccharose, sodium chloride, grape sugar, urea, starch, calcium carbonate, kaoline, crystalline cellulose, or silica; binders such as water, ethanol, propanol, simple syrup, grape sugar in water, starch solution, gelatin solution, carboxymethyl cellulose, shellac, methylcellulose, potassium phosphate, or polyvinyl pyrrolidone; disintegrators such as dry starch, sodium alginate, agar powder, laminaran powder, sodium bicarbonate, calcium carbonate, polyoxyethylene sorbitan fatty acid esters, sodium lauryl sulfate, monoglyceride stearate, starch, or lactose; disintegration inhibitors such as saccharose, stearin, cacao butter, or hydrogenated oil; absorbefacients such as quaternary ammonium base or sodium lauryl sulfate; humectant such as glycerin or starch; adsorbents such as starch, lactose, kaoline, bentonite, or colloidal silica; and lubricants such as purified talc, stearate, boric acid powder, or polyethylene glycol. Such a tablet may be further processed into a tablet coated with an ordinary tablet coat, such as a sugarcoated tablet, a gelatin-coated tablet, an enteric-coated tablet, a film-coated tablet, a double-coated tablet, and a multiple layer tablet, as necessary. When the present tetomilast crystal is molded into the form of a pill, carriers, which have previously been known in the present field, can widely be used. Examples of such a carrier that can be used herein may include: excipients such as grape sugar, lactose, starch, cacao butter, hydrogenated vegetable oil, kaoline, or talc; binders such as gum Arabic, powdered tragacanth, gelatin, or ethanol; and disintegrators such as laminaran or agar. When the present tetomilast crystal is molded into the form of a suppository, carriers, which have previously been known in the present field, can widely be used. Examples of such a carrier may include polyethylene glycol, cacao butter, higher alcohol, higher alcohol esters, gelatin, and semisynthetic glyceride. As a capsule, an active ingredient compound is generally mixed with various types of carriers as described above according to a common method, and the obtained mixture is then filled into a hard gelatin capsule, a soft capsule, etc. When the present tetomilast crystal is molded into an injection, it is preferable that a liquid agent, an emulsion, and a suspension be sterilized and be isotonic to blood. When the present crystal is molded into such a form, all types of diluents, which have commonly been used in the present field, can be used. Examples of such diluents that can be used herein may include water, ethyl alcohol, macrogol, propylene glycol, ethoxylated isostearyl alcohol, polyoxylated isostearyl alcohol, and polyoxyethylene sorbitan fatty acid esters. In this case, it is possible that common salt, grape sugar, or glycerin, be mixed into a pharmaceutical preparation in an amount sufficient to prepare an isotonic solution. It is also possible that a common solubilizer, buffer, soothing agent, or the like, be added to the pharmaceutical preparation. Further, it is also possible that a coloring agent, a preservative, an aromatic, a flavor, a sweetener, or other pharmaceuticals, be mixed into the pharmaceutical preparation, as necessary.

The amount of an active ingredient compound contained in the above pharmaceutical preparation is not particularly limited, and it is appropriately selected from a wide range. In general, approximately 1% to 70% by weight of such an active ingredient compound may be contained in the preparation.

The administration method of the above pharmaceutical preparation is not particularly limited, and the pharmaceutical preparation is administered by a method that depends on various types of pharmaceutical forms, the age, sex, and other conditions of a patient, the degree of disease, etc. For example, in the case of a tablet, a pill, solution, suspension, emulsion, a granule, and a capsule, these preparations are orally administered. In the case of injection, it is intravenously administered singly or as a mixture with an ordinary replacement fluid such as grape sugar or amino acid. Further, as necessary, such injection is administered as a single use, intramuscularly, intradermally, subcutaneously, or intraperitoneally. A suppository is administered intrarectally.

The dosage of the above pharmaceutical preparation is appropriately selected depending on usage, the age, sex, and other conditions of a patient, the degree of disease, etc. In general, the amount of an active ingredient compound may be determined to be approximately 0.2 to 200 mg per kg of body weight per day.

With regard to the tetomilast hydrate crystal, anhydrous tetomilast type A crystal, anhydrous tetomilast type C crystal, tetomilast acetonitrile solvate crystal, and a mixture of the above anhydrous tetomilast type A crystal and an anhydrous tetomilast type B crystal of the present invention, the crystal forms thereof are easily controlled by recrystallization, and these crystals are excellent in terms of filterability. Thus, these crystals are suitable for industrial mass production.

In addition, these tetomilast crystals have performance that is equivalent to or greater than that of an anhydrous tetomilast type B crystal, in terms of stability towards heat and moisture, and the disintegration property and dissolution property of tablets. Accordingly, these tetomilast crystals can preferably be used as pharmaceutical compositions.

EXAMPLES

The present invention will be described more in detail in the following reference examples, examples, and formulation example.
Analytical Method
(1) Thermogravimetry/Differential Thermal Analysis
Thermogravimetry/differential thermal analysis was carried out using TA60WS controller and DTG-60A thermogravimetry/differential thermal analysis simultaneous measuring instrument manufactured by Shimadzu Corporation. Specifically, using the aforementioned apparatuses, 5 to 10 mg of a sample was heated from 20° C. (room temperature) to 250° C. at a temperature-rising rate of 5° C./min in a dry nitrogen atmosphere. As a reference substance, α-alumina was used.
(2) Powder X-ray Diffraction
The powder X-ray diffraction spectrum was measured in an angle of diffraction that ranged from 3° to 40°, according to the general test method of the Pharmacopoeia of Japan, using RAD-2B diffractometer (radiation source: CuKα) manufactured by Rigaku Denki. During the measurement, voltage/current was set at 35 kV/20 mA, and the scan speed was set at 5°/min.

The mixing ratio of a mixture consisting of an anhydrous tetomilast type A crystal and an anhydrous tetomilast type B crystal was obtained by comparing the powder X-ray diffraction spectrum of the above mixture, with the powder X-ray diffraction spectrum of a mixture formed by mixing a pure anhydrous tetomilast type A crystal and a pure anhydrous tetomilast type B crystal at various ratios.
(3) Infrared Spectroscopic Analysis
The IR spectrum was measured by the KBr method.
(4) $^1$H-NMR Measurement
The $^1$H-NMR spectrum was measured in DMSO-$d_6$, using TMS as a reference.
(5) Purity Measurement
The purity was measured using high performance liquid chromatography (HPLC). The measurement conditions were as follows.
Sample: 0.03 g of a sample was dissolved in 80 ml of acetonitrile, and 20 ml of water was then added to the solution, so as to prepare a sample solution. The measurement was carried out using 10 μl of the sample solution.
Detector: Ultraviolet photometric detector (UV 254 nm)
Column: Wakosil 5C18 HG
Mobile phase: Acetonitrile/10 mM $Na_2SO_4$ aqueous solution/phosphoric acid (500:500:1)
(6) Particle Size Measurement
For the measurement of the particle size, 0.1 g of particles to be measured was suspended in 20 ml of n-hexane solution that contained 0.2 g of 0.1 w/v % polyoxyethylene (10) octylphenyl ether, and ultrasonication was then performed on the suspension. Thereafter, the measurement was carried out using a particle size distribution measurement equipment (Microtrac HRA; manufactured by Microtrac).
(7) Moisture Value Measurement
The moisture contained in the sample was measured by the Karl Fischer method.
(8) Melting Point Measurement (Corrected)
For the measurement of the melting point, the sample was heated using a heater (product name: LK6000PM; manufactured by Japan High Tech Co., Ltd.) under the condition of a temperature-rising rate of 5° C./rain, and the melting state was then observed using a VH-7000C microscope manufactured by Keyence Corporation.

Reference Example 1

Production of Anhydrous Tetomilast Type B Crystal
An anhydrous tetomilast type B crystal was produced by the methods described in (1) to (3) below.
(1) An anhydrous tetomilast type B crystal was obtained by the method described in Journal of Medicinal Chemistry, 1995, 38, pp. 353-358. That is to say, an anhydrous tetomilast type B crystal was obtained by the following method.

First, methyl 6-[2-(3,4-diethoxyphenyl)thiazol-4-yl]pyridin-2-carboxylate (49 g; 127 mmol) and 10% sodium hydroxide (100 ml) were added to ethanol (1.4 L), and the obtained mixture was then stirred for 4 hours under heating to reflux. A majority of solvent was eliminated from the obtained solution, and water and ethyl acetate were then added to the residue for separation. The water layer obtained as a result of the separation was changed to acidic by addition of 10% hydrochloric acid, followed by extraction with ethyl acetate. Thereafter, the extract was quickly washed with a saturated sodium chloride aqueous solution, and was then dried over an excessive amount of magnesium sulfate. The obtained mixture was recrystallized from ethyl acetate, so as to obtain an anhydrous tetomilast type B crystal.

A part of the obtained anhydrous tetomilast type B crystal melted around 175° C., and it was changed to a needle crystal. Thereafter, the above crystal completely melted (decomposed) at a temperature between 187° C. and 190° C.

The obtained anhydrous tetomilast type B crystal was subjected to thermogravimetry/differential thermal analysis. As a result, it was found that the same endothermic peaks as those shown in FIG. 5 were observed.

The powder X-ray diffraction spectrum of the obtained anhydrous tetomilast type B crystal was measured. As a result, it was found that the same spectrum as that shown in FIG. 6 was observed.

The IR(KBr) spectrum of the obtained anhydrous tetomilast type B crystal was measured. As a result, it was found that the obtained anhydrous tetomilast type B crystal had significant infrared absorption bands at 3298, 3090, 1744, 1593, 1474, 1348, 1269, 1132, 1045, 762, and 706 $cm^{-1}$ in the IR (KBr) spectrum thereof.

(2) 5 g of an anhydrous tetomilast type A crystal obtained by the method of Example 1 as described later was dissolved in 400 ml of isopropanol while stirring under heating to reflux. The obtained solution was cooled to approximately 30° C. over about 1 hour, and it was then further cooled at 10° C. or lower for 1 hour, so as to obtain the precipitated crystal by filtration. The above precipitated crystal was dried at 50° C. for 3 hours, so as to obtain 4.6 g of an anhydrous tetomilast type B crystal in the form of a while needle crystal (yield: 92%).

A part of the obtained anhydrous tetomilast type B crystal melted around 175° C., and it was changed to a needle crystal. Thereafter, the above crystal completely melted (decomposed) at a temperature between 187° C. and 190° C.

The obtained anhydrous tetomilast type B crystal was subjected to thermogravimetry/differential thermal analysis. As a result, it was found that as shown in FIG. 5, endothermic peaks were observed around 177° C. and 188° C.

The powder X-ray diffraction spectrum of the obtained anhydrous tetomilast type B crystal was measured. As a result, it was found that as shown in FIG. 6, the above crystal had characteristic peaks at 2θ=4.1°, 8.1°, 11.9°, 16.1°, and 24.2°.

The IR(KBr) spectrum of the obtained anhydrous tetomilast type B crystal was measured. As a result, it was found that the obtained anhydrous tetomilast type B crystal had significant infrared absorption bands at 3298, 3090, 1744, 1593, 1474, 1348, 1269, 1132, 1045, 762, and 706 $cm^{-1}$ in the IR (KBr) spectrum thereof.

(3) 10 g of an anhydrous tetomilast type A crystal obtained by the method of Example 1 as described later was dissolved in 400 ml of ethyl acetate while stirring under heating to reflux. The obtained solution was cooled to approximately 30° C. over about 1 hour, and it was then further cooled at 10° C. or lower for 1 hour, so as to obtain the precipitated crystal by filtration. The above precipitated crystal was dried at 50° C. for 3 hours, so as to obtain 9.3 g of an anhydrous tetomilast type B crystal in the form of a while needle crystal (yield: 93%).

A part of the obtained anhydrous tetomilast type B crystal melted around 175° C., and it was changed to a needle crystal. Thereafter, the above crystal completely melted (decomposed) at a temperature between 187° C. and 190° C.

The obtained anhydrous tetomilast type B crystal was subjected to thermogravimetry/differential thermal analysis. As a result, it was found that the same endothermic peaks as those shown in FIG. 5 were observed.

The powder X-ray diffraction spectrum of the obtained anhydrous tetomilast type B crystal was measured. As a result, it was found that the same spectrum as that shown in FIG. 6 was observed.

The IR(KBr) spectrum of the obtained anhydrous tetomilast type B crystal was measured. As a result, it was found that the obtained anhydrous tetomilast type B crystal had significant infrared absorption bands at 3298, 3090, 1744, 1593, 1474, 1348, 1269, 1132, 1045, 762, and 706 $cm^{-1}$ in the IR (KBr) spectrum thereof.

Example 1

Production of Anhydrous Tetomilast Type A Crystal

An anhydrous tetomilast type A crystal was produced by the methods described in (1) to (7) below.

(1) 5 g of the anhydrous tetomilast type B crystal obtained in Reference example 1 (3) was dissolved in a solution consisting of 140 ml of acetone and 35 ml of water, while stirring under heating to reflux. The obtained solution was cooled to 40° C. over about 100 minutes (at this point, an anhydrous tetomilast type A crystal was precipitated), and it was then further cooled to 10° C. or lower, so as to obtain the precipitated crystal by filtration. The above precipitated crystal was dried at 60° C. for 18 hours, so as to obtain 4.0 g of an anhydrous tetomilast type A crystal in the form of a while columnar crystal (yield: 80%).

The obtained anhydrous tetomilast type A crystal melted (decomposed) at a temperature between 187° C. and 189° C.

The obtained anhydrous tetomilast type A crystal was subjected to thermogravimetry/differential thermal analysis. As a result, it was found that as shown in FIG. 3, an endothermic peak was observed around 188° C.

The powder X-ray diffraction spectrum of the obtained anhydrous tetomilast type A crystal was measured. As a result, it was found that as shown in FIG. 4, the above crystal had characteristic peaks at 2θ=10.5°, 13.1°, 18.4°, 21.9°, and 25.8°.

The IR(KBr) spectrum of the obtained anhydrous tetomilast type A crystal was measured. As a result, it was found that the obtained anhydrous tetomilast type A crystal had significant infrared absorption bands at 3306, 3084, 1746, 1593, 1474, 1348, 1271, 1132, 1045, 758, and 704 $cm^{-1}$ in the IR (KBr) spectrum thereof.

(2) 5 g of the anhydrous tetomilast type A crystal obtained in Example 1 (6) as described later was dissolved in 400 ml of ethanol while stirring under heating to reflux. The obtained solution was cooled to approximately 30° C. over about 1 hour, and it was then further cooled at 10° C. or lower for 1 hour, so as to obtain the precipitated crystal by filtration. The above precipitated crystal was dried at 50° C. for 3 hours, so as to obtain 4.3 g of an anhydrous tetomilast type A crystal in the form of a while columnar crystal (yield: 86%).

The melting point of the obtained anhydrous tetomilast type A crystal was between 188° C. and 190° C. (decomposition).

The obtained anhydrous tetomilast type A crystal was subjected to thermogravimetry/differential thermal analysis. As a result, it was found that the same endothermic peak as that shown in FIG. 3 was observed.

The powder X-ray diffraction spectrum of the obtained anhydrous tetomilast type A crystal was measured. As a result, it was found that the same spectrum as that shown in FIG. 4 was observed.

The IR(KBr) spectrum of the obtained anhydrous tetomilast type A crystal was measured. As a result, it was found that the obtained anhydrous tetomilast type A crystal had significant infrared absorption bands at 3306, 3084, 1746, 1593, 1474, 1348, 1271, 1132, 1045, 758, and 704 $cm^{-1}$ in the IR (KBr) spectrum thereof.

(3) 10 g of the anhydrous tetomilast type A crystal obtained in Example 1 (6) as described later was dissolved in 400 ml of acetone while stirring under heating to reflux. The obtained solution was cooled to approximately 30° C. over about 1 hour, and it was then further cooled at 10° C. or lower for 1 hour, so as to obtain the precipitated crystal by filtration. The above precipitated crystal was dried at 50° C. for 3 hours, so as to obtain 8.3 g of an anhydrous tetomilast type A crystal in the form of a while columnar crystal (yield: 83%).

The obtained anhydrous tetomilast type A crystal melted (decomposed) at a temperature between 188° C. and 190° C.

The obtained anhydrous tetomilast type A crystal was subjected to thermogravimetry/differential thermal analysis. As a result, it was found that the same endothermic peak as that shown in FIG. 3 was observed.

The powder X-ray diffraction spectrum of the obtained anhydrous tetomilast type A crystal was measured. As a result, it was found that the same spectrum as that shown in FIG. 4 was observed.

The IR(KBr) spectrum of the obtained anhydrous tetomilast type A crystal was measured. As a result, it was found that the obtained anhydrous tetomilast type A crystal had significant infrared absorption bands at 3306, 3084, 1746, 1593, 1474, 1348, 1271, 1132, 1045, 758, and 704 $cm^{-1}$ in the IR (KBr) spectrum thereof.

(4) 10 g of the anhydrous tetomilast type A crystal obtained in Example 1 (6) as described later was dissolved in a solution consisting of 320 ml of acetone and 80 ml of water, while stirring under heating to reflux. The obtained solution was cooled, in a stepwise manner, to 30° C. over about 3 hours, it was then cooled to 20° C. over 1 hour, and it was then further cooled to 10° C. over 0.5 hours, so as to obtain the precipitated crystal by filtration. The above precipitated crystal was dried at 50° C. for 3 hours, so as to obtain 8.3 g of an anhydrous tetomilast type A crystal in the form of a while columnar crystal (yield: 83%).

The obtained anhydrous tetomilast type A crystal melted (decomposed) at a temperature between 187° C. and 189° C.

The obtained anhydrous tetomilast type A crystal was subjected to thermogravimetry/differential thermal analysis. As a result, it was found that the same endothermic peak as that shown in FIG. 3 was observed.

The powder X-ray diffraction spectrum of the obtained anhydrous tetomilast type A crystal was measured. As a result, it was found that the same spectrum as that shown in FIG. 4 was observed.

The IR(KBr) spectrum of the obtained anhydrous tetomilast type A crystal was measured. As a result, it was found that the obtained anhydrous tetomilast type A crystal had significant infrared absorption bands at 3306, 3084, 1746, 1593, 1474, 1348, 1271, 1132, 1045, 758, and 704 $cm^{-1}$ in the IR (KBr) spectrum thereof.

(5) 5 g of the anhydrous tetomilast type A crystal obtained in Example 1 (6) as described later was dissolved in a solution consisting of 450 ml of acetone and 300 ml of water, while stirring under heating to reflux. The obtained solution was cooled to approximately 30° C. over about 1 hour, and it was then further cooled at 10° C. or lower for 1 hour, so as to obtain the precipitated crystal by filtration. The above precipitated crystal was dried at 50° C. for 3 hours, so as to obtain 4.2 g of an anhydrous tetomilast type A crystal in the form of a while columnar crystal (yield: 84%).

The obtained anhydrous tetomilast type A crystal melted (decomposed) at a temperature between 188° C. and 190° C.

The obtained anhydrous tetomilast type A crystal was subjected to thermogravimetry/differential thermal analysis. As a result, it was found that the same endothermic peak as that shown in FIG. 3 was observed.

The powder X-ray diffraction spectrum of the obtained anhydrous tetomilast type A crystal was measured. As a result, it was found that the same spectrum as that shown in FIG. 4 was observed.

The IR(KBr) spectrum of the obtained anhydrous tetomilast type A crystal was measured. As a result, it was found that the obtained anhydrous tetomilast type A crystal had significant infrared absorption bands at 3306, 3084, 1746, 1593, 1474, 1348, 1271, 1132, 1045, 758, and 704 $cm^{-1}$ in the IR (KBr) spectrum thereof.

(6) 41.4 g of ethyl 3-oxo-3-(6-methoxycarbonyl-2-pyridyl)propionate was dissolved in a solution consisting of 42 ml of water and 414 ml of ethyl acetate, and the obtained solution was then cooled to a temperature between 5° C. and 10° C. Thereafter, a solution obtained by dissolving 35.6 g of sulfuryl chloride in 83 ml of ethyl acetate was added dropwise to the above cooled solution over approximately 30 minutes, while stirring. Thereafter, the obtained mixture was stirred at a temperature between 10° C. and 20° C. for 1 hour. Subsequently, the reaction solution was heated up to approximately 90° C., while the solvent was distilled away from the reaction solution. The reaction solution was continuously heated at a temperature between approximately 90° C. and 100° C. for 2 hours while stirring. Thereafter, the obtained mixed suspension (containing crystals) was cooled to approximately 10° C., and it was then stirred for 1 hour, followed by filtration, so as to obtain 27.99 g of 2-(2-chloroacetyl)-6-pyridine carboxylic acid in the form of yellow-brown crystals (melting point: 184° C. to 189° C.; purity: 98% to 99%).

20 g of 2-(2-chloroacetyl)-6-pyridine carboxylic acid and 22.6 g of 3,4-diethoxythiobenzamide were dissolved in a solution consisting of 100 ml of water and 200 ml of dimethoxyethane. The obtained solution was heated to reflux for 2 hours while stirring, and the reaction solution was then cooled to 5° C. or lower, so as to obtain a yellow-brown precipitate by filtration:

Subsequently, the above precipitated crystal was dissolved in a solution formed by dissolving 6.18 g of potassium hydroxide in 372 ml of water. The obtained solution was extracted with ethyl acetate twice (186 ml×2). Thereafter, 1 g of activated carbon was added to the separated water layer, and the obtained solution was then stirred at approximately 30° C. for 30 minutes. Thereafter, the activated carbon was removed by filtration, and 372 ml of acetone and 11.2 g of concentrated hydrochloric acid were then added to the obtained filtrate, so as to obtain a suspension (a mixture consisting of a tetomilast hydrate crystal and an anhydrous tetomilast type B crystal). In order to transfer the mixture consisting of a tetomilast hydrate crystal and an anhydrous tetomilast type B crystal to an anhydrous tetomilast type A crystal, the above suspension was heated at 60° C. for 30 minutes, and it was then cooled to room temperature, so as to obtain a crystal by filtration, thereby obtaining an anhydrous tetomilast type A crude crystal (34.82 g; wet state).

8.67 g of the crude crystal was dissolved in a solution consisting of 213 ml of acetone and 53 ml of water by heating at 60° C. without drying it, followed by filtration during a hot state. Subsequently, the obtained filtrate was heated again, and dissolution of the crystal was then confirmed. Thereafter, the filtrate was cooled to 50° C. 79 mg of an anhydrous tetomilast type A crystal was added as a seed crystal to the cooled filtrate, and the obtained mixture was then stirred at a temperature between 42° C. and 50° C. (internal temperature) for 2 hours. Thereafter, the obtained solution was cooled to 20° C. over approximately 20 minutes, and it was then stirred at a temperature between 19° C. and 25° C. for 2 hours. Thereafter, the solution was cooled to 5° C. over 35 minutes, and it was then stirred at a temperature between 4° C. and 5° C. for 2 hours, so as to obtain the precipitated crystal by filtration. The above precipitated crystal was dried at 80° C. overnight, so as to obtain 7.25 g of an anhydrous tetomilast type A crystal (whose yield was 78.4% when 6-chloroacetyl-2-pyridine carboxylic acid was used as a reference). The HPLC purity of the obtained anhydrous tetomilast type A crystal was 99.9%.

A part of the obtained anhydrous tetomilast type A crystal melted (decomposed) at a temperature between 187° C. and 189° C.

The obtained anhydrous tetomilast type A crystal was subjected to thermogravimetry/differential thermal analysis. As a result, it was found that the same endothermic peak as that shown in FIG. 3 was observed.

The powder X-ray diffraction spectrum of the obtained anhydrous tetomilast type A crystal was measured. As a result, it was found that the same spectrum as that shown in FIG. 4 was observed.

The IR(KBr) spectrum of the obtained anhydrous tetomilast type A crystal was measured. As a result, it was found that the obtained anhydrous tetomilast type A crystal had significant infrared absorption bands at 3306, 3084, 1746, 1593, 1474, 1348, 1271, 1132, 1045, 758, and 704 cm$^{-1}$ in the IR (KBr) spectrum thereof.

The obtained anhydrous tetomilast type A crystal was crushed with an atomizer, so as to obtain powders having a mean particle size of 30.4 μm and a 90% cumulative particle size of 57 μm.

(7) 32.36 g of the tetomilast hydrate crude crystal obtained in Example 5 (2) as described later was dissolved in a solution consisting of 197 ml of purified water and 793 ml of acetone by heating at approximately 60° C., followed by filtration during a hot state. Subsequently, the obtained filtrate was heated again, and dissolution of the crystal was then confirmed. Thereafter, the filtrate was cooled to 45° C. 290 mg of an anhydrous tetomilast type A crystal was added to the cooled filtrate, and the obtained mixture was then stirred at 45° C. for 2 hours. Thereafter, the obtained solution was cooled to 20° C. over about 1 hour, and it was then stirred at a temperature between 20° C. and 24° C. for 2 hours. Thereafter, the solution was cooled to 5° C. over about 2 hours, and it was then stirred at a temperature between −1° C. and 5° C. for 2 hours, so as to obtain the precipitated crystal by filtration. The above precipitated crystal was dried at 80° C. for 4 hours, so as to obtain 24.11 g of an anhydrous tetomilast type A crystal.

The obtained anhydrous tetomilast type A crystal was subjected to thermogravimetry/differential thermal analysis. As a result, it was found that the same endothermic peak as that shown in FIG. 3 was observed.

The powder X-ray diffraction spectrum of the obtained anhydrous tetomilast type A crystal was measured. As a result, it was found that the same spectrum as that shown in FIG. 4 was observed.

The IR(KBr) spectrum of the obtained anhydrous tetomilast type A crystal was measured. As a result, it was found that the obtained anhydrous tetomilast type A crystal had significant infrared absorption bands at 3306, 3084, 1746, 1593, 1474, 1348, 1271, 1132, 1045, 758, and 704 cm$^{-1}$ in the IR (KBr) spectrum thereof.

Example 2

Production of Anhydrous Tetomilast Type C Crystal 5 g of the anhydrous tetomilast type A crystal obtained in Example 1 (6) was dissolved in 500 ml of methanol, while stirring under heating to reflux. The obtained solution was cooled to approximately 30° C. over about 1 hour, and it was then further cooled at 10° C. or lower for 1 hour, so as to obtain the precipitated crystal by filtration. The above precipitated crystal was dried at 50° C. for 3 hours, so as to obtain 3.8 g of an anhydrous tetomilast type C crystal in the form of a while platy crystal (yield: 76%).

A needle crystal was generated from the crystal surface of the obtained anhydrous tetomilast type C crystal at 184° C., and the above crystal melted (decomposed) at a temperature between 187° C. and 190° C.

The obtained anhydrous tetomilast type C crystal was subjected to thermogravimetry/differential thermal analysis. As a result, it was found that as shown in FIG. 7, endothermic peaks were observed around 184° C. and around 189° C.

The powder X-ray diffraction spectrum of the obtained anhydrous tetomilast type C crystal was measured. As a result, it was found that as shown in FIG. 8, the above crystal had characteristic peaks at 2θ=4.2°, 8.2°, 12.0°, 16.4°, 24.7°, and 25.9°.

The IR(KBr) spectrum of the obtained anhydrous tetomilast type A crystal was measured. As a result, it was found that the obtained anhydrous tetomilast type A crystal had significant infrared absorption bands at 3300, 3088, 1744, 1593, 1476, 1346, 1267, 1132, 1045, 754, and 704 cm$^{-1}$ in the IR (KBr) spectrum thereof.

Example 3

Production of Tetomilast Acetonitrile Solvate Crystal 5 g of the anhydrous tetomilast type A crystal obtained in Example 1 (6) was dissolved in 400 ml of acetonitrile, while stirring under heating to reflux. The obtained solution was cooled to approximately 30° C. over about 1 hour, and it was then further cooled at 10° C. or lower for 1 hour, so as to obtain the precipitated crystal by filtration. The above precipitated crystal was dried at 50° C. for 3 hours, so as to obtain 5.1 g of a tetomilast acetonitrile solvate crystal in the form of a while platy crystal (yield: quantitative).

The obtained tetomilast acetonitrile solvate crystal became clouded at 90° C., and the above crystal melted (decomposed) at a temperature between 187° C. and 190° C.

The obtained tetomilast acetonitrile solvate crystal was subjected to thermogravimetry/differential thermal analysis. As a result, it was found that as shown in FIG. 9, endothermic peaks were observed around 91° C., around 176° C., and around 189° C.

The powder X-ray diffraction spectrum of the obtained tetomilast acetonitrile solvate crystal was measured. As a result, it was found that as shown in FIG. 10, the above crystal had characteristic peaks at 2θ=3.6°, 7.1°, 10.6°, 14.2°, and 24.8°.

The IR(KBr) spectrum of the obtained tetomilast acetonitrile solvate crystal was measured. As a result, it was found that the obtained tetomilast acetonitrile solvate crystal had significant infrared absorption bands at 3300, 3090, 2249 (nitrile group), 1744, 1593, 1476, 1346, 1269, 1132, 1045, 752, and 704 cm$^{-1}$ in the IR (KBr) spectrum thereof.

The NMR (DMSO-$d_6$) spectrum of the obtained tetomilast acetonitrile solvate crystal was measured.

As a result, it was found that a methyl group peak of acetonitrile was observed at δ2.1 ppm.

Example 4

Production of Mixture Consisting of Anhydrous Tetomilast Type A Crystal and Anhydrous Tetomilast Type B Crystal A mixture consisting of an anhydrous tetomilast type A crystal and an anhydrous tetomilast type B crystal was produced by the method described in (1) or (2) below:

(1) 10 g of the anhydrous tetomilast type A crystal obtained in Example 1 (6) was dissolved in a solution consisting of 320 ml of acetone and 80 ml of water, while stirring under heating to reflux. The obtained solution was cooled to approximately 30° C. over about 1 hour, and it was then cooled to 10° C. over about 10 minutes. Thereafter, the solution was further cooled at 10° C. or lower for 1 hour, so as to obtain the precipitated crystal by filtration. The above precipitated crystal was dried at 50° C. for 3 hours, so as to obtain 8.5 g of a mixture consisting of an anhydrous tetomilast type A crystal and an anhydrous tetomilast type B crystal (A:B=40:60) in the form of a while columnar crystal (yield: 85%).

Only a small part of the obtained mixture consisting of an anhydrous tetomilast type A crystal and an anhydrous tetomilast type B crystal melted at 178° C., and it was crystallized in the form of a needle crystal. Thereafter, the mixture melted (decomposed) at a temperature between 188° C. and 190° C.

The obtained mixture consisting of an anhydrous tetomilast type A crystal and an anhydrous tetomilast type B crystal (A:B=40:60) was subjected to thermogravimetry/differential thermal analysis. As a result, it was found that as shown in FIG. 11, endothermic peaks were observed around 175° C. and around 189° C.

In addition, the powder X-ray diffraction spectrum of the obtained mixture consisting of an anhydrous tetomilast type A crystal and an anhydrous tetomilast type B crystal (A:B=40:60) was measured.

As a result, it was found that as shown in FIG. 12, the above mixture had characteristic peaks at 2θ=4.2°, 11.9°, 13.2°, 16.2°, 17.3°, 24.3°, 25.3°, 25.9°, and 27.5°.

Moreover, the IR(KBr) spectrum of the obtained mixture consisting of an anhydrous tetomilast type A crystal and an anhydrous tetomilast type B crystal (A:B=40:60) was measured. As a result, it was found that the obtained mixture had significant infrared absorption bands at 3298, 3088, 1744, 1593, 1474, 1348, 1269, 1132, 1045, 760, and 704 cm$^{-1}$ in the IR (KBr) spectrum thereof.

(2) 10 g of the anhydrous tetomilast type A crystal obtained in Example 1 (6) was dissolved in a solution consisting of 320 ml of acetone and 80 ml of water, while stirring under heating to reflux. The obtained solution was quenched to 10° C. over 30 minutes, so as to obtain the precipitated crystal by filtration. The above precipitated crystal was dried at 50° C. for 3 hours, so as to obtain 7.8 g of a mixture consisting of an anhydrous tetomilast type A crystal and an anhydrous tetomilast type B crystal (A:B=10:90) in the form of while powders yield: 78%). A part of the obtained mixture melted at 176° C., and it was crystallized in the form of a needle crystal. Thereafter, the mixture melted (decomposed) at a temperature between 187° C. and 190° C.

The obtained mixture consisting of an anhydrous tetomilast type A crystal and an anhydrous tetomilast type B crystal (A:B=10:90) was subjected to thermogravimetry/differential thermal analysis. As a result, it was found that as shown in FIG. 13, endothermic peaks were observed around 176° C. and around 189° C.

The powder X-ray diffraction spectrum of the obtained mixture consisting of an anhydrous tetomilast type A crystal and an anhydrous tetomilast type B crystal (A:B=10:90) was measured. As a result, it was found that as shown in FIG. 14, the above mixture had characteristic peaks at 2θ=4.1°, 11.9°, 16.1°, 17.2°, 19.3°, 24.2°, 25.1°, 25.9°, and 27.3°.

The IR(KBr) spectrum of the obtained mixture consisting of an anhydrous tetomilast type A crystal and an anhydrous tetomilast type B crystal (A:B=10:90) was measured. As a result, it was found that the obtained mixture had significant infrared absorption bands at 3298, 3090, 1744, 1593, 1474, 1348, 1269, 1132, 1045, 756, and 706 cm$^{-1}$ in the IR (KBr) spectrum thereof.

Example 5

Production of Tetomilast Monohydrate Crystal

A tetomilast monohydrate crystal was produced by the methods described in (1) to (3) below:

(1) 18.7 g of 2-(2-chloroacetyl)-6-pyridine carboxylic acid and 21.1 g of 3,4-diethoxythiobenzamide were dissolved in a solution consisting of 94 ml of water and 187 ml of dimethoxyethane, and the obtained mixture was then stirred at approximately 80° C. (reflux) for 2 hours. The obtained solution was cooled to 5° C., and it was then stirred for 1 hour, so as to obtain a yellow-brown precipitate by filtration. The above precipitate was dissolved in a solution formed by dissolving 5.78 g of potassium hydroxide in 348 ml of water. The obtained mixture solution was washed with 174 ml of ethyl acetate twice. Thereafter, a solution formed by suspending 0.9 g of activated carbon in 1.9 ml of water was added to the separated water layer, and the obtained mixture was then stirred at a temperature between 30° C. and 31° C. for 30 minutes. Thereafter, the activated carbon was removed by filtration, and 348 ml of acetone was then added to the obtained filtrate. Subsequently, 10.4 g of concentrated hydrochloric acid was added thereto while stirring, and the obtained mixture was then stirred for 1 hour. Thereafter, the precipitated crystal was collected by filtration. This crystal was suspended in 348 ml of water, and the obtained mixture was then stirred at a temperature between 27° C. and 30° C. for 30 minutes. Thereafter, the obtained crystal was collected by filtration. The obtained crystal was washed with a solution consisting of 35 ml of acetone and 35 ml of water, so as to obtain 29.53 g of a tetomilast monohydrate crystal.

The obtained tetomilast monohydrate crystal was subjected to thermogravimetry/differential thermal analysis. As a result, as shown in FIG. 1, an endothermic peak was observed around 189° C., and further, a wide peak was observed around 102° C.

The powder X-ray diffraction spectrum of the obtained tetomilast monohydrate crystal was measured.

As a result, as shown in FIG. 2, it was found that the above crystal had characteristic peaks at 2θ=10.6°, 12.9°, 21.1°, 22.3°, and 25.0°.

The IR(KBr) spectrum of the obtained tetomilast monohydrate crystal was measured. As a result, it was found that the obtained crystal had significant infrared absorption bands at 3516, 3433, 1742, 1709, 1587, 1472, 1267, 1143, 1040, 758, and 716 cm$^{-1}$ in the IR (KBr) spectrum thereof.

(2) 50 g of the anhydrous tetomilast type A crystal obtained in Example 1 (6) was dissolved in a solution formed by dissolving 8.33 g of potassium hydroxide in 500 ml of water. This solution was filtrated, and 500 ml of acetone was then added to the obtained filtrate. Thereafter, 13 ml (1.1 eq) of concentrated hydrochloric acid was added thereto while stirring (The product precipitated at that time was an anhydrous tetomilast type B crystal). The obtained solution was stirred at room temperature for approximately 10 minutes. After completion of the stirring, 2.5 g of the tetomilast monohydrate crystal obtained in the aforementioned Example 5 (1) was added as a seed crystal to the resultant, and the obtained mixture was continuously stirred for 2 hours (During such stirring, transformation progressed via the solvent. If the stirring time was short, a mixture consisting of a tetomilast hydrate crystal and an anhydrous tetomilast type B crystal was obtained.) The precipitated crystal was collected by filtration, and the obtained crystal was then suspended in 400 ml of water. The obtained mixture was stirred at a temperature between 20° C. and 30° C. for 30 minutes. Thereafter, the crystal was collected by filtration, and it was then washed with 80 ml of acetone-water (an acetone content of 50% by volume). The resultant was dried under reduced pressure all night, so as to obtain 51.5 g of a tetomilast monohydrate crystal.

The obtained tetomilast monohydrate crystal was subjected to thermogravimetry/differential thermal analysis. As a result, the same endothermic peak as that shown in FIG. 1 was obtained.

The powder X-ray diffraction spectrum of the obtained tetomilast monohydrate crystal was measured. As a result, the same spectrum as that shown in FIG. 2 was observed.

The IR(KBr) spectrum of the obtained tetomilast monohydrate crystal was measured. As a result, it was found that the obtained crystal had significant infrared absorption bands at 3516, 3433, 1742, 1709, 1587, 1472, 1267, 1143, 1040, 758, and 716 cm$^{-1}$ in the IR (KBr) spectrum thereof.

(3) 2.37 g of the anhydrous tetomilast type B crystal obtained in Reference example 1(3) was suspended in a solution consisting of 50 ml of acetone and 50 ml of water, and the obtained mixture was then stirred for approximately 5 minutes. Thereafter, a tetomilast hydrate crystal was added as a seed crystal to the above mixture, and the thus obtained mixture was further stirred at 30° C. for 1 hour. The crystal was collected by filtration, and it was then dried at 60° C. all night, so as to obtain 2.34 g of a tetomilast hydrate crystal.

The moisture value of the obtained tetomilast hydrate crystal was 4.68%. This value was almost the same as the theoretical moisture value (4.64%) of a tetomilast monohydrate crystal.

The above monohydrate became clouded around 100° C., and melted (decomposed) at a temperature between 188° C. and 189° C.

The obtained tetomilast monohydrate crystal was subjected to thermogravimetry/differential thermal analysis. As a result, the same endothermic peak as that shown in FIG. 1 was obtained.

The powder X-ray diffraction spectrum of the obtained tetomilast monohydrate crystal was measured. As a result, the same spectrum as that shown in FIG. 2 was observed.

The IR(KBr) spectrum of the obtained tetomilast monohydrate crystal was measured. As a result, it was found that the obtained crystal had significant infrared absorption bands at 3516, 3433, 1742, 1709, 1587, 1472, 1267, 1143, 1040, 758, and 716 cm$^{-1}$ in the IR (KBr) spectrum thereof.

Example 6

Thermal Transformation from Anhydrous Tetomilast Type B Crystal to Anhydrous Tetomilast Type A Crystal Thermal transformation from an anhydrous tetomilast type B crystal to an anhydrous tetomilast type A crystal was confirmed by the means described in (1) to (3) below:

(1) The anhydrous tetomilast type B crystal obtained in Reference example 1 (3) was left at a temperature between 20° C. and 30° C. for approximately 1 year, and thereafter, the crystal form thereof was examined by powder X-ray diffraction. As a result, it was confirmed that the above crystal maintained the form as an anhydrous tetomilast type B crystal.

(2) 5 g of the anhydrous tetomilast type B crystal obtained in Reference example 1 (3) was suspended in a solution consisting of 40 ml of acetone and 10 ml of water, and the obtained mixture was then stirred at 20° C. At that time, sampling was carried out at intervals of 15 minutes, 30 minutes, 60 minutes, and 120 minutes, and each of the obtained samples was subjected to powder X-ray diffraction to examine the crystal form. As a result, it could be confirmed that each of the samples collected after stirring for 15 minutes, 30 minutes, and 60 minutes, maintained the form as an anhydrous tetomilast type B crystal.

On the other hand, it could be confirmed that the sample collected after stirring for 120 minutes was a mixture consisting of an anhydrous tetomilast type B crystal and an anhydrous tetomilast type A crystal (A:B=70:30).

(3) 5 g of the anhydrous tetomilast type B crystal obtained in Reference example 1 (3) was suspended in a solution consisting of 40 ml of acetone and 10 ml of water, and the obtained mixture was then stirred at 40° C. At that time, sampling was carried out at intervals of 15 minutes, 30 minutes, 60 minutes, and 120 minutes, and each of the obtained samples was subjected to powder X-ray diffraction to examine the crystal form. As a result, it could be confirmed that the sample collected after stirring for 15 minutes was a mixture consisting of an anhydrous tetomilast type B crystal and an anhydrous tetomilast type A crystal (A:B=50:50).

On the other hand, it could be confirmed that each of the samples that had been stirred for 30 minutes, 60 minutes, and 120 minutes, was changed to an anhydrous tetomilast type A crystal.

When tetomilast crystals with different crystal forms are obtained depending on the type of a solvent used, the obtained crystal forms do not depend on the crystal forms of tetomilast crystals used as raw materials. Thus, an example of using an anhydrous tetomilast type A crystal (purity of 99.9%) was given herein. When a novel tetomilast crystal other than the anhydrous tetomilast type A crystal was used as well, the same results were obtained.

Formulation Example

A table comprising 5 mg of an anhydrous tetomilast type C crystal, 132 mg of starch, 18 mg of magnesium stearate and 45 mg of lactose, in a single tablet, was produced by a common method.

The invention claimed is:

1. An anhydrous tetomilast type A crystal having a powder X-ray diffraction spectrum that is substantially the same as the powder X-ray diffraction spectrum shown in FIG. 4.

2. An anhydrous tetomilast type A crystal having a powder X-ray diffraction spectrum having characteristic peaks at 2θ=10.5°, 13.1°, 18.4°, 21.9°, and 25.8°.

3. A process for the preparation of an anhydrous tetomilast type A crystal as defined in claim 1 or 2, wherein it comprises recrystallization from a solution formed by dissolving an anhydrous tetomilast type B crystal in ethanol or acetone, wherein said anhydrous tetomilast type B crystal has a powder X-ray diffraction spectrum shown in FIG. 6.

4. A process for the preparation of an anhydrous tetomilast type A crystal as defined in claim 1 or 2, wherein it comprises dissolving an anhydrous tetomilast type B crystal in a mixture of acetone and water wherein the acetone content is 40% or more by volume, followed by retaining the obtained solution at 40° C. to 50° C. for 60 minutes or longer, and then cooling the solution in order to obtain the anhydrous tetomilast type A crystal, wherein said anhydrous tetomilast type B crystal has a powder X-ray diffraction spectrum shown in FIG. 6.

5. A process for the preparation of an anhydrous tetomilast type A crystal as defined in claim 1 or 2, wherein it comprises stirring from a suspension formed by suspending at least one type of tetomilast crystal selected from the group consisting of a tetomilast hydrate crystal, an anhydrous tetomilast type B crystal, an anhydrous tetomilast type C crystal, and a tetomilast acetonitrile solvate crystal in a mixed solvent consisting of water and at least one organic solvent selected from the group consisting of methanol, ethanol, acetone, and tetrahydrofuran, wherein the temperature of the suspension is between 0 and 65° C. and the stirring time is between 10 minutes to 48 hours,
wherein said tetomilast hydrate crystal has a powder X-ray diffraction spectrum shown in FIG. 2, wherein said anhydrous tetomilast type B crystal has a powder X-ray diffraction spectrum shown in FIG. 6, wherein said anhydrous tetomilast type C crystal has a powder X-ray diffraction spectrum shown in FIG. 8, wherein said tetomilast acetonitrile solvate crystal has a powder X-ray diffraction spectrum shown in FIG. 10.

6. A process for the preparation of an anhydrous tetomilast type A crystal as defined in claim 1 or 2, wherein it comprises recrystallization from a solution formed by dissolving an anhydrous tetomilast type B crystal in ethanol or acetone, wherein said anhydrous tetomilast type B crystal has a powder X-ray diffraction spectrum having characteristic peaks at 2θ=4.1°, 8.1°, 11.9°, 16.1°, and 24.2°.

7. A process for the preparation of an anhydrous tetomilast type A crystal as defined in claim 1 or 2, wherein it comprises dissolving an anhydrous tetomilast type B crystal in a mixture of acetone and water wherein the acetone content is 40% or more by volume, followed by retaining the obtained solution at 40° C. to 50° C. for 60 minutes or longer, and then cooling the solution in order to obtain the anhydrous tetomilast type A crystal, wherein said anhydrous tetomilast type B crystal has a powder X-ray diffraction spectrum having characteristic peaks at 2θ=4.1°, 8.1°, 11.9°, 16.1°, and 24.2°.

8. A process for the preparation of an anhydrous tetomilast type A crystal as defined in claim 1 or 2, wherein it comprises stirring from a suspension-formed by suspending at least one type of tetomilast crystal selected from the group consisting of a tetomilast hydrate crystal, an anhydrous tetomilast type B crystal, an anhydrous tetomilast type C crystal, and a tetomilast acetonitrile solvate crystal in a mixed solvent consisting of water and at least one organic solvent selected from the group consisting of methanol, ethanol, acetone, and tetrahydrofuran, wherein the temperature of the suspension is between 0 and 65° C. and the stirring time is between 10 minutes to 48 hours,
wherein said tetomilast hydrate crystal has a powder X-ray diffraction spectrum having characteristic peaks at 2θ=10.6°, 12.9°, 21.1°, 22.3°, and 25.0°, wherein said anhydrous tetomilast type B crystal has a powder X-ray diffraction spectrum having characteristic peaks at 2θ=4.1°, 8.1°, 11.9°, 16.1°, and 24.2°, wherein said anhydrous tetomilast type C crystal has a powder X-ray diffraction spectrum having characteristic peaks at 2θ=4.2°, 8.2°, 12.0° , 16.4°, 24.7°, and 25.9°, wherein said tetomilast acetonitrile solvate crystal has a powder X-ray diffraction spectrum having characteristic peaks at 2θ=3.6°, 7.1°, 10.6°, 14.2°, and 24.8°.

9. A process for the preparation of an anhydrous tetomilast type A crystal as defined in claim 1 or 2, wherein it comprises recrystallization from a solution formed by dissolving an anhydrous tetomilast type B crystal having a powder X-ray diffraction spectrum that is substantially the same as the powder X-ray diffraction spectrum shown in FIG. 6 in acetone and then decreasing the temperature of the solution at rate of 0.8° C/min or less.

10. A process for the preparation of an anhydrous tetomilast type A crystal as defined in claim 1 or 2, wherein it comprises recrystallization from a solution formed by dissolving an anhydrous tetomilast type B crystal having a powder X-ray diffraction spectrum that is substantially the same as the powder X-ray diffraction spectrum having characteristic peaks at 2θ=4.1°, 8.1°, 11.9°, 16.1° and 24.2° in acetone and then decreasing the temperature of the solution at rate of 0.8° C/min or less.

11. A process for the preparation of an anhydrous tetomilast type A crystal as defined in claim 1 or 2, wherein it comprises recrystallization from a solution formed by dissolving an anhydrous tetomilast type B crystal in acetone, wherein said anhydrous tetornlast type B crystal has a powder X-ray diffraction spectrum shown in FIG. 6.

12. A process for the preparation of an anhydrous tetomilast type A crystal as defined in claim 1 or 2, wherein it comprises recrystallization from a solution formed by dissolving an anhydrous tetomilast type B crystal in acetone, wherein said anhydrous tetomilast type B crystal has a powder X-ray diffraction spectrum having characteristic peaks at 2θ=4.1°, 8.1°, 11.9°, 16.1° and 24.2°.

13. A process for the preparation of an anhydrous tetomilast type A crystal as defined in claim 1 or 2, wherein it comprises stirring from a suspension formed by suspending at least one type of tetomilast crystal selected from the group consisting of a tetomilast hydrate crystal having a powder X-ray diffraction spectrum that is substantially the same as the powder X-ray diffraction spectrum shown in FIG. 2, an anhydrous tetomilast type C crystal having a powder X-ray diffraction spectrum that is substantially the same as the powder X-ray diffraction spectrum shown in FIG. 8 and a tetomilast acetonitrile solvate crystal having a powder X-ray diffraction spectrum that is substantially the same as the powder X-ray diffraction spectrum shown in FIG. 10 or a mixture of anhydrous tetomilast type B crystal and a tetomilast hydrate crystal in a mixed solvent consisting of water and at least one organic solvent selected from the group consisting of methanol, ethanol, acetone, and tetrahydrofuran, wherein the temperature of the suspension is between 0 and 65° C. and the stirring time is between 10 minutes to 48 hours, wherein said anhydrous tetomilast type B crystal has a powder X-ray diffraction spectrum shown in FIG. 6.

14. A process for the preparation of an anhydrous tetomilast type A crystal as defined in claim 1 or 2, which is characterized in that it comprises stirring from a suspension formed by suspending at least one type of tetomilast crystal selected from the group consisting of a tetomilast hydrate crystal having a powder x-ray diffraction spectrum having characteristic peaks at 2θ=10.6°, 12.9°, 21.1°, 22.3° and 25.0°, tetomilast type C crystal as defined having a powder X-ray diffraction spectrum having characteristic peaks at 2θ=4.2°, 8.2°, 12.0°, 16.4°, 24.7° and 25.9° and a tetomilast acetonitrile solvate crystal having a powder X-ray diffraction spectrum that is substantially the same as the powder X-ray diffraction spectrum having characteristic peaks at 2θ=3.6°, 7.1°, 10.6°, 14.2° and 24.8° or a mixture of an anhydrous tetomilast type B crystal and a tetomilast hydrate crystal in a mixed solvent consisting of water and at least one organic solvent selected from the group consisting of methanol, ethanol, acetone, and tetrahydrofuran, wherein the temperature of the suspension is between 0 and 65° C. and the stirring time is between 10 minutes and 48 hours, wherein said anhydrous tetomilast type B crystal has a powder X-ray diffraction spectrum having characteristic peaks at 2θ=4.1°, 8.1°, 11.9°, 16.1° and 24.2°.

* * * * *

UNITED STATES PATENT AND TRADEMARK OFFICE
CERTIFICATE OF CORRECTION

| | | |
|---|---|---|
| PATENT NO. | : 8,501,949 B2 | Page 1 of 1 |
| APPLICATION NO. | : 12/086587 | |
| DATED | : August 6, 2013 | |
| INVENTOR(S) | : Aoki et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1307 days.

Signed and Sealed this
Thirteenth Day of January, 2015

Michelle K. Lee
*Deputy Director of the United States Patent and Trademark Office*